US011752179B2

(12) United States Patent
Biffi et al.

(10) Patent No.: US 11,752,179 B2
(45) Date of Patent: *Sep. 12, 2023

(54) MEDICAL USE OF PROBIOTICS

(71) Applicant: ALFASIGMA S.P.A., Bologna (IT)

(72) Inventors: Andrea Biffi, Urgnano (IT); Walter Fiore, Atrani (IT); Ruggero Rossi, Milan (IT)

(73) Assignee: ALFASIGMA S.P.A., Bologna (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/308,330

(22) PCT Filed: Jun. 8, 2017

(86) PCT No.: PCT/IB2017/053389
§ 371 (c)(1),
(2) Date: Dec. 7, 2018

(87) PCT Pub. No.: WO2017/212433
PCT Pub. Date: Dec. 14, 2017

(65) Prior Publication Data
US 2019/0290706 A1    Sep. 26, 2019

(30) Foreign Application Priority Data
Jun. 8, 2016  (IT) .................. 102016000058515

(51) Int. Cl.
*A61K 35/747* (2015.01)
*A61K 36/064* (2006.01)
*A61P 1/00* (2006.01)
*A61K 9/14* (2006.01)
*A61K 9/20* (2006.01)
*A61K 9/48* (2006.01)
*A61K 9/00* (2006.01)
*A61K 35/745* (2015.01)

(52) U.S. Cl.
CPC .......... *A61K 35/747* (2013.01); *A61K 9/0014* (2013.01); *A61K 9/0053* (2013.01); *A61K 35/745* (2013.01); *A61K 36/064* (2013.01); *A61P 1/00* (2018.01)

(58) Field of Classification Search
CPC .. A61K 35/747; A61K 9/0014; A61K 9/0053; A61K 35/745; A61K 36/064; A61P 1/00
See application file for complete search history.

(56) References Cited

U.S. PATENT DOCUMENTS

| | | |
|---|---|---|
| 5,531,989 A | 7/1996 | Paul |
| 5,716,615 A | 2/1998 | Cavaliere Vesely et al. |
| 6,770,246 B1 | 8/2004 | Husek |
| 7,510,734 B2 | 3/2009 | Sullivan et al. |
| 11,400,124 B2 | 8/2022 | Biffi |
| 11,464,814 B2 | 10/2022 | Biffi |
| 11,591,416 B2 | 2/2023 | Biffi et al. |
| 2002/0090416 A1 | 7/2002 | Connolly |
| 2003/0031659 A1 | 2/2003 | Farmer |
| 2003/0092163 A1 | 5/2003 | Collins et al. |
| 2003/0157146 A1 | 8/2003 | Rautonen et al. |
| 2003/0190369 A1 | 10/2003 | Lovett |
| 2004/0170617 A1 | 9/2004 | Finegold |
| 2005/0196480 A1 | 9/2005 | Sullivan et al. |
| 2006/0057704 A1 | 3/2006 | Schlothauer et al. |
| 2006/0067921 A1 | 3/2006 | Conway |
| 2008/0081035 A1 | 4/2008 | Parmely et al. |
| 2008/0193603 A1 | 8/2008 | Hayes et al. |
| 2008/0241226 A1 | 10/2008 | Abeln et al. |
| 2009/0061446 A1 | 3/2009 | Niimi et al. |
| 2009/0098088 A1 | 4/2009 | Taylor et al. |
| 2009/0220481 A1 | 9/2009 | Maes et al. |
| 2009/0274662 A1* | 11/2009 | Magowan ............ A61K 31/635 424/93.4 |
| 2009/0312282 A1 | 12/2009 | Yoshida et al. |
| 2010/0074994 A1 | 3/2010 | Harel et al. |
| 2010/0112564 A1 | 5/2010 | Zhao et al. |
| 2011/0014167 A1 | 1/2011 | Bindels et al. |
| 2011/0038837 A1 | 2/2011 | Nishida et al. |
| 2011/0052538 A1 | 3/2011 | Brown et al. |
| 2011/0166100 A1 | 7/2011 | Wu |
| 2011/0305744 A1 | 12/2011 | Russo |
| 2012/0251512 A1 | 10/2012 | Farmer et al. |
| 2012/0269865 A1 | 10/2012 | Roughead et al. |
| 2012/0301451 A1 | 11/2012 | Braenning et al. |

(Continued)

FOREIGN PATENT DOCUMENTS

| | | |
|---|---|---|
| CN | 1161795 A | 10/1997 |
| CN | 1701116 A | 11/2005 |
| CN | 1840206 A | 10/2006 |
| CN | 101636173 A | 1/2010 |

(Continued)

OTHER PUBLICATIONS

Intermountain Healthcare. 2015. Irritable Bowel Syndrome (IBS). Retrieved from: https://intermountainhealthcare.org/services/gastroenterology/conditions/irritable-bowel-syndrome/ (Year: 2015).*
Guo, Y. et al. 2014. Irritable Bowel Syndrome is Positively Related to Metabolic Syndrome: A Population-Based Cross-Sectional Study. PLoS One. 9(11): e112289. (Year: 2014).*
Crohn's and Colitis Foundation of America. 2014. Inflammatory Bowel Disease and Inflammatory Bowel Syndrome: Similarities and Differences. (Year: 2014).*
Patel et al., Clinical Infectious Diseases, vol. 60, Supplement 2, S108-121 (Year: 2015).*
Guglielmetti et al., "Randomised clinical trial: Bifidobacterium bifidum MIMBb75 significantly alleviates irritable bowel syndrome and improves quality of life—a double-blind, placebo-controlled study," Aliment Pharmacol Ther 33: 1123-1132 (2011).

(Continued)

*Primary Examiner* — Michelle F. Paguio Frising
(74) *Attorney, Agent, or Firm* — Steinfl + Bruno LLP

(57) ABSTRACT

The present invention relates to the use of a composition based on bacteria and/or yeasts and/or other microorganisms, taken singularly or in combination, for the treatment of abdominal pain by administering to a patient suffering from Irritable Bowel Syndrome (IBS). In particular, the bacteria comprise *Lactobacillus paracasei* DG strain deposited with the deposit number CNCMI 1572.

16 Claims, 5 Drawing Sheets

(56) References Cited

U.S. PATENT DOCUMENTS

| | | | |
|---|---|---|---|
| 2012/0322773 | A1 | 12/2012 | Pravda |
| 2016/0296569 | A1* | 10/2016 | Guglielmetti ......... A23L 33/135 |
| 2016/0348155 | A1* | 12/2016 | Guglielmetti ........ A61K 35/747 |
| 2017/0035816 | A1* | 2/2017 | Biffi ..................... A61K 35/747 |
| 2017/0202231 | A1 | 7/2017 | Budelli et al. |
| 2019/0192590 | A1* | 6/2019 | Biffi ........................ A23L 33/16 |
| 2019/0345268 | A1 | 11/2019 | Biffi et al. |
| 2021/0186075 | A1 | 6/2021 | Biffi et al. |
| 2021/0236565 | A1 | 8/2021 | Biffi |
| 2022/0325234 | A1 | 10/2022 | Biffi et al. |
| 2022/0339216 | A1 | 10/2022 | Biffi et al. |
| 2022/0354910 | A1 | 11/2022 | Biffi et al. |
| 2022/0370520 | A1 | 11/2022 | Biffi et al. |
| 2022/0409676 | A1 | 12/2022 | Biffi et al. |
| 2023/0052820 | A1 | 2/2023 | Biffi |

FOREIGN PATENT DOCUMENTS

| | | |
|---|---|---|
| CN | 102919922 A | 2/2013 |
| CN | 103997899 A | 8/2014 |
| CN | 108743851 A | 11/2018 |
| CN | 109310719 A | 2/2019 |
| EP | 1145643 A1 | 10/2001 |
| EP | 2407532 A2 | 1/2012 |
| JP | H0517363 A | 1/1993 |
| JP | 2005508617 A | 4/2005 |
| JP | 2005534315 A | 11/2005 |
| JP | 2010512755 A | 4/2010 |
| JP | 2010161944 A | 7/2010 |
| JP | 2013515051 A | 5/2013 |
| RU | 2182008 C1 | 5/2002 |
| WO | 00/54788 A1 | 9/2000 |
| WO | 2003/090763 A1 | 11/2003 |
| WO | 2004/022727 A1 | 3/2004 |
| WO | 2005/001109 A2 | 1/2005 |
| WO | 2005/083122 A2 | 9/2005 |
| WO | 2006/050479 A2 | 5/2006 |
| WO | 2007/071815 A1 | 6/2007 |
| WO | 2007/140621 A1 | 12/2007 |
| WO | 2008/119012 A2 | 10/2008 |
| WO | 2008/148798 A2 | 12/2008 |
| WO | 2010/008272 A1 | 1/2010 |
| WO | 2010/008278 A1 | 1/2010 |
| WO | 2010/099824 A1 | 9/2010 |
| WO | 2011/036539 A1 | 3/2011 |
| WO | 2012/154738 A1 | 11/2012 |
| WO | 2014/068338 A1 | 5/2014 |
| WO | 2014/137211 A1 | 9/2014 |
| WO | 2015/000972 A1 | 1/2015 |
| WO | 2015/033304 A1 | 3/2015 |
| WO | 2015/033305 A1 | 3/2015 |
| WO | 2015/162570 A1 | 10/2015 |
| WO | 2015/172191 A1 | 11/2015 |
| WO | 2016/030320 A1 | 3/2016 |
| WO | 2017/195182 A1 | 11/2017 |
| WO | 2017/212433 A1 | 12/2017 |
| WO | 2018/100549 A1 | 6/2018 |
| WO | 2018/109520 A1 | 6/2018 |
| WO | 2018/109730 A1 | 6/2018 |
| WO | 2019/019961 A1 | 1/2019 |
| WO | 2019/053604 A1 | 3/2019 |
| WO | 2019/111189 A1 | 6/2019 |
| WO | 2021/053636 A1 | 3/2021 |
| WO | 2021/053639 A1 | 3/2021 |
| WO | 2021/053641 A2 | 3/2021 |
| WO | 2021/053642 A1 | 3/2021 |
| WO | 2021/090228 A1 | 5/2021 |
| WO | 2021/090228 A4 | 7/2021 |

OTHER PUBLICATIONS

Ng et al., "Effect of probiotic bacteria on the intestinal micobiota in irritable bowel syndrome," Journal of Gastroenterology and Hepatology 28: 1624-1631 (2013).

U.S. National Library of Medicine, "Efficacy Evaluation of a Commercial Preparation Containing Lactobacillus Casei DG on the Reduction of the Painful Symptoms Related to the Irritable Bowel Syndrome (IBS). A Pilot Clinical Study," ClinicalTrials.gov (https://clinicaltrials.gov/show/NCT02077699) (2014).

U.S. National Library of Medicine, "Effect of Lactobacillus Casei DG (Enterolactis Plus) in Patient With Irritable Bowel Syndrome: a Pilot Study," ClinicalTrials.gov (https://clinicaltrials.gov/ct2/show/NCT02371499) (2015).

Spiller et al., "Randomized double blind placebo-controlled trial of *Saccharomyces cerevisia* CNCM I-3856 in Irritable bowel syndrome: improvement in abdominal pain and bloating in those with predominant constipation," United European Gastroenterology Journal 4: 353-362 (2016).

Ausubel et al, Current Protocols In molecular biology, edited vols. 1 and 2. John Wiley & Sons, Inc., Media, PA, 2003.

Balzaretti et al., "A Novel rhamnose-rich heterp-exopolysaccharide isolated from Lactobacillus paracasei DG activates THP-1 human monocytic cells"*University of Huddersfiled Repository Article for Applied and Environmental Microbiology*.Jan. 17, 2017.

Balzaretti et al., "Exploring Lactobacillus paracasei probiosis and metabolic potential", University of Milan PhD thesis, 2015, pp. 1-132.

Ciucanu I. et al. "A simple and rapid method for the permethylation of carbohydrates" *Carbohydrate Research*, (1984) pp. 209-217.

Collins M.N. and Birkinshaw C. "Hyaluronic acid based scaffolds for tissue engineering—A review", Carbohydrate Polymers 2013, 1262-1279.

Communication pursuant to Article 94(3) EPC for EP Application No. 14790322.3 filed on Sep. 5, 2014 on behalf of SOFAR S.P.A. dated Jan. 31, 2020 8 pages.

De Souza M.M. et aJ. "Effects of budesonide and probiotics enemas on the systemic inflammatory response of rats with experimental coJitis", Acta Cirurgica Brasileira 2007, 22 (Supp 1. 1 ): 40-45.

Di Mario Francesco et al., "Use of mesalazine in diverticular disease." Journal of Clinical Gastroenterology. vol. 40, Suppl 3, Aug. 2006.

D'Inca R. et al. Rectal administration of Lactobacillus Casei DG modifies flora composition and Toll-Like receptor expression in colonic mucosa of patients with mildulcerative colitis'\ Dig. Dis. Sci. 2011, 56:1178-1187. European Food Safety Authority.

EFSA Journal, "Scientific Opinion on the maintenance of the list of QPS biological agents intentionally added to food and feed (2012 update)1" EFSA Journal2012; 10(12):3020. 84 pages.

European Food Safety Authority EFSA journal (2012) 10(6): 2723.

Evans S. "Clinical trial structures" *J Exp Stroke Transl Med*.Mar. 2011, pp. 1-16, 16 pages.

"Example Cross-Over Study Design {A Phase 11, Randomized, Double-Blind Crossover Study of Hypertena and Placebo in Participants with High Blookd Pressure)". ClinicalTrials.gov (2012).

Fakhari A. and Berkland C. "Applications and emerging trends of hyaluronic acid in tissue engineering, as a dermal filler and in osteoarthritis treatment", Acta Biomaterialia2013, 9, 7081-7092.

Fao and Who et al; "Live microorganisms which, when administered in adequate amounts, confer a health benefit on the host", *World Health Organizations and Food Agriculture Organization*. 2001.

Farup et al., "Probiotics, Symptoms, and Gut Microbiota; What are the relations? A Randomized Controlled Trial in Subjects with Irritable Bowel Syndrome" Gastro Research and Practice, vol. 2012. 7 pages.

Ferrario et al. J. Nutrition (published online Sep. 3, 2014) 144:1787-1796 (Year: 2014).

Final Office Action for U.S. Appl. No. 14/916,959, filed Mar. 4, 2016 on behalf of SOFAR SPA. dated Jul. 23, 2019. 23 pages.

Final Office Action for U.S. Appl. No. 14/916,961, filed Mar. 4, 2016 on behalf of SOFAR S.P.A dated Jan. 2, 2020 16 pages.

Final Office Action for U.S. Appl. No. 14/916,961, filed Mar. 4, 2016 on behalf of SOFAR S.P.A. dated Mar. 13, 2018. 15 pages.

Final Office Action for U.S. Appl. No. 15/305,470, filed Oct. 20, 2016 on behalf of SOFAR SPA. dated Jan. 14, 2019. 10 pages.

Final Office Action for U.S. Appl. No. 14/916,959, filed Mar. 4, 2016 on behalf of SOFAR SPA. dated Apr. 20, 2018. 26 pages.

(56) References Cited

OTHER PUBLICATIONS

Fiorino et al., "P325 Efficacy and Safety of IBD98E, a Sodium Hyaluronate Topical Preparation, in the Induction of Clinical and Endoscopic Remission in Patients with Distal Ulcerative Colitis: An Open Label Study," United European Gastroenterology Journal: 1(1S) (A219), (2013).
Floch M.H. et al. "Recommendations for probiotic use—2011 Update", J. Clin.Gastroenterol.2011, 45: S168-S171.
Food and Agriculture Organization. Health and nutritional properties of probiotics in food including powder milk with live lactic acid bacteria.Oct. 2001: 34 pages.
Gerwig G. et al., "Determination of the absolute configuration of mono-saccharides in complex carbohydrates by capillary G.L.C." *Carbohydrate Research*,77(1979) pp. 1-7.
Gill et al., "Metagenomic Analysis of the Human Distal Gut Microbiome," Science 312: 1355-1359 (2006).
Guglielmetti S. et al., "TgaA, a VirB1-Like Component Belonging to a Putative Type IV Secretion System of Bifidobacterium bifidum MIMBb75" *Applied and Environmental Microbiology*,vol. 80, No. 17,Sep. 2014 pp. 5161-5169.
Havea P. "Protein interactions in milk protein concentrate powders" *International Dairy Journal*,vol. 16,2006, pp. 415-422.
International Search Report for International Application No. PCT/IB2014/064284 filed on Sep. 5, 2014 on behalf of SOFAR SPA. dated Jan. 26, 2015. 6 pages.
International Search Report for International Application No. PCT/IB2014/064285 filed on Sep. 5, 2014 on behalf of SOFAR SPA. dated Jan. 29, 2015. 4 pages.
International Search Report for International Application No. PCT/IB2017/052850 filed on May 15, 2017 on behalf of SOFAR SPA. dated Aug. 17, 2017. 4 pages.
International Search Report for International Application No. PCT/IB2017/053389 filed on Jun. 8, 2017 on behalf of SOFAR SPA. dated Oct. 6, 2017. 5 pages.
International Search Report for International Application No. PCT/IB2017/057576 filed on Dec. 1, 2017 on behalf of SOFAR SPA. dated Feb. 22, 2018. 5 pages.
International Search Report for International Application No. PCT/IB2017/057980 filed on Dec. 15, 2017 on behalf of SOFAR SPA. dated Mar. 19, 2018. 4 pages.
International Search report for International Application PCT/IB2015/052938 filed on Apr. 22, 2015 on behalf of SOFAR SPA. dated Jul. 31, 2015. 4 pages.
Italia il Ministero della Salute ( *Linee Guida su Probiotici e Prebiotici rev*.May 2013).
Jacobsen et al., "Screening of Probiotic Activities of Forty-Seven Strains of *Lactobacillus* spp. By In Vitro techniques and Evaluation of the Colonization Ability of Five Selected Strains in Humans" Applied and Environmental Microbiology, Nov. 1999, p. 4949-4956. 8 pages.
Larsen et al., "Predominant genera of fecal microbiota in children with atopic dermatitis are not altered by intake of probiolic bacteria Lactobacillus acidophilus NCFM and *Bifidobacterium animalis* subsp. lacis Bi-07," FEMS Microbiol Ecol 75: 482-496 (2011).
Laws et al., "Biosynthesis, characterization, and design of bacterial exopolysacharides from lactic acid bacteria",*Biotechnology Advances*. vol. 19,2001. pp. 597-625.
LeBlanc et al., "Beneficial effects on host energy metabolism of shot-chain fatty acids and vitamins produced by commensal and probiotic bacteria," Microbial Cell Factories 16:79: 1-10 (2017).
Lombardo L; et al "New insights into Lactobacillus and functional intestinal disorders", Minerva Gastroenterologica E Dietologica, Edizioni Minerva Medica, Torino, IT, vol. 54, No. 3. 2008.
Lombardo, Lucio et al., "Clinical Evaluation of *Lactobacillus paracasei* Subsp. Paracasei F19 with Gluco-Oligosaccharides in the Short-term Treatment of liritable Bowel Syndrome" Microbial Ecology in Health and Disease 21: 28-32 (2009).
Martin R. et al. "Role of commensal and probiotic bacteria in human health: a focus on inflammatory bowel disease", Microbial Cell Factories2013, 12: 71.

Matthes H. et al. "Clinical trial: probiotic treatment of acute distal ulcerative colitis with rectally administered *Escherichia Coli* Nissle 1917 (EcN)", BMC Complementaty and Alternative Medicine2010, 10:13.
Mazzuoli S. et al. "Definition and evaluation of mucosal healing in clinical practice", Digestive and Liver Disease2013, 45, 969-977.
Michail et al., "Gut Microbiota is Not Modified by Randmized, Double-Blind, Placebo-Controlled Trial of VSL#3 in Diarrhea-Predominant Irritable Bowel Syndrome". (Probiotics & Antimicro Prot. (2011) 3: 1-7).
Milani et al., Assessing the fecal microbiota: and optimized ion torrent 16S rRNA genebased analysis protocol. PLoS One. 2013; 8(7); e68739, 12 pages. Published2013.
Montalto M. et al., "Clinical trial: the effects of a probiotic mixture on non-steroidal anti-inflammatory drug enteropathy—a randomized, double-blind, cross-over, placebo-controlled study" *Aliment Pharmacol Ther*,2010, pp. 209-214, 6 pages.
Muyzer et al., "Profiling of Complex Microbial Populations by Denaturing Gradient Gel Electrophoresis Analysis of Polymerase Chain Reaction-Amplified Genes Coding for 16S rRNA," Applied and Environmental Microbiology 59:595-700(1993).
Necas J. et al. "Hyaluronic acid (hyaluronan): a review", Veterinarni Medicina, 2008, 53(8): 397-411.
Neiwert et al., "Structural Investigation of rhamnose-rich polysaccharides from *Streptococcus* dysgalactiae bovine mastitis Isolate" Carbohydrate Research, vol. 389,2014. pp. 192-195.
Non-Final Office Action for U.S. Appl. No. 14/916,961, filed Mar. 4, 2016 on behalf of SOFAR S.P.A. dated Jun. 30, 2017. 21 pages.
Non-Final Office Action for U.S. Appl. No. 14/916,961, filed Mar. 4, 2016 on behalf of SOFAR S.P.A. dated Jul. 25, 2019. 18 pages.
Non-Final Office Action for U.S. Appl. No. 15/305,470, filed Oct. 20, 2016 on behalf of SOFAR SPA. dated Aug. 22, 2019. 8 pages.
Non-Final Office Action for U.S. Appl. No. 16/301,361, filed Nov. 13, 2018 on behalf of SOFAR S.P.A. dated May 8, 2020 20 pages.
Non-Final Office Action for U.S. Appl. No. 14/916,959, filed Mar. 4, 2016 on behalf of SOFAR S.P.A. dated Mar. 13, 2020 25 pages.
Non-Final Office Action for U.S. Appl. No. 14/916,959, filed Mar. 4, 2016 on behalf of SOFAR SPA. dated Aug. 31, 2017. 27 pages.
Non-Final Office Action for U.S. Appl. No. 14/916,959, filed Mar. 4, 2016 on behalf of SOFAR SPA. dated Nov. 19, 2018. 15 pages.
Non-Final Office Action for U.S. Appl. No. 15/305,470, filed Oct. 20, 2016 on behalf of SOFAR SPA. dated Mar. 26, 2018. 10 pages.
Office Action in corresponding Chinese Patent Application No. 201480049296.4, dated Aug. 27, 2019.
Office Action in Corresponding Japanese Patent Application No. 2016-564193, dated Apr. 2, 2019.
Okuda et al., "Virtual metagenome reconstruction from 16S rRNA gene sequences".*Nature Communications*,2012. 8 pages.
Oliva S. et al. "Randomised clinical trial: the effectiveness of Lactobacillus Reuteri ATCC 55730 rectal enema in children with active distal ulcerative colitis", Aliment. Pharmacol. Ther.2012, 35:327-334.
Olveira et al; "Lactobacillus paracasei Reduces Intestinal Inflammation in Adoptive Transfer Mouse Model of Experimental Colitis", Clinical and Developmenta Immunology, vol. 23, No. 5, Jan. 1, 2011, pp. 1077-13.
Orlando A. et al. "Clinical implications of mucosal healing in the management of patients with inflammatory bowel disease", Digestive and Liver Disease2013, 45, 986-991.
Plant et al., "Association of *Lactobacillus* spp. with Peyer's Patches in Mice", Clinical and Diagnostic Laboratory Immunology 8: 320-324 (2001).
Polak-Berecka et al., "Physlocochemical characterization of exopolysaccharides produced by lactobacillus rhamnosus on various carbon sources", Carbohydrate Polymers, vol. 117, 2015. pp. 501-509.
Price R.D. et al. "Hyaluronic acid: the scientific and clinical evidence", Journal ofPlastic, Reconstructive & Aesthetic Surgery2007, 60: 1110-1119.
Restriction Requirement for U.S. Appl. No. 14/916,961, filed Mar. 4, 2016 on behalf of SOFAR S.P.A. dated May 10, 2019. 7 pages.
Sambrook et al. Molecular cloning: A Laboratory Manual. 3rd ed., vols. 1, 2 and 3 cold Spring Harbor Laboratory Press,2001, 2100 pp.

(56) References Cited

OTHER PUBLICATIONS

Sanlibaba et al., "Exopolysaccharides production by lactic acid bacteria",*Applied Microbiology*, vol. 2,May 20, 2016.
Sasaki M. et al., "Transglucosidase improves the gut microbiota profile of type 2 diabetes mellitus patients: a randomized double-blind, placebo-controlled study" *BMC Gastroenterology*, 13:81,2013.
Savino et al., "Laclobacillus reuteri DSM 17938 in Infantile Colic: A Randomized, Double-Blind, Placebo-Controlled Trial", Pediatrics 126: e526-e533 (2010).
Scaldaferri F. et al. "Gut microbial flora, prebiotics and probiotics in IBD: their current usage and utility", BioMed Research International2013, 9 pages.
Stuknyte M. et al., "Potential immunomodulatory activity of bovine casein hydrolysates produced after digestion with proteinases of lactic acid bacteria" *International Dairy Journal*, 21(2011) pp. 763-769.
Taverniti and Gugliemetti et al., "The immunomodulatory properties of probiotic microorganisms beyond their viability (ghost probiotics: proposal of paraprobiotic concept)".
Turnbaugh et al., "The Effect of Diel on the Human Gut Microbiome: A Metagenomic Analysis in Humanized gnolobiotic Mice," Sci Transl Med: (2009).
Tursi et al., "Balsalazide and/or high-potency probiotic mixture (VSL#3) in maintaining remission after attack of acute, uncomplicated diverticulitis of the colon", International Journal of Colorectal Disease; Clinical and Molecular Gastroenterology an Surgery, Sprinter, Berlin, DE. Vol. 22, No. 9,Mar. 28, 2007. pp. 1103-1108.
Tursi et al., "Effect of Lactobacillus casei supplementation on the effectiveness and tolerability of a new second-line 10-day quadruple therapy after failure of a first attempt to cure Helicobacter pylori infection," Med Sci Monit 10: CR662-666 (2004).
Tursi et al., "Mesalazine and/or Lactobacillus Casei in maintaining Long-term Remission of Symptomatic Uncomplicated Diverticular Disease of the Colon" Original Paper. Hepato-Gastroenterology. 2008, 55; 916-920.
Tursi et al., "Mesalazine and/or Lactobacillus casei in preventing recurrence of symptomatic uncomplicated diverticular disease of the colon: A Prospective , randomized, open-label study", Journal of Clinical Gastroenterol, Raven Press Ltd, NY, New York. vol. 40, No. 2, Apr. 1, 2006. pp 312-316.
Tursi et al., "Randomised clinical trial: mesalazine and/or probiotics in maintaining remission of symptomatic uncomplicated diverticula disease—double-blind, randomized, placebo-controlled study" Alimentary Pharmacology & Therapeutics. vol. 38, No. 7.Oct. 19, 2013. pp. 741-751.
Valerio et al., "Effects of Probiotic Lactobacillus paracasei-enriched Artichokes on Constipated Patients", J Clin Gastroenterol,Sep. 10, 2010.
Vernia et al. Dig. Disease Sci. (1988) 33(11): 1353-135 (Year: 1988).
Vinogradov et al., "Structural studies of the rhamnoselrch cell wall polysaccharide of lactobacillus casei BL23"*Carbohydrate Research* vol. 435,Oct. 8, 2016. pp. 156-161.
"Why VSL#3" (Obtained from https://vsl3.com/hcp/vsl-info on Aug. 22, 2017, 4 pages.
Worthley et al. "A human, double-blind, placebo-controlled, crossover trial of prebiotic, probiotic, and symbiotic supplementation: effects on luminal, inflammatory, epigenetic, and epithelial biomarkers of colorectal cancer" (Am J Clin Nutr 2009; 90; 578-86).
Written Opinion for International Application No. PCT/IB2014/ 064284 filed on Sep. 5, 2014 on behalf of SOFAR SPA. dated Jan. 26, 2015. 7 pages.
Written Opinion for International Application No. PCT/IB2014/ 064285 filed on Sep. 5, 2014 on behalf of SOFAR SPA. dated Jan. 29, 2015. 7 pages.
Written Opinion for International Application No. PCT/IB2017/ 052850 filed on May 15, 2017 on behalf of SOFAR SPA. dated Aug. 17, 2017. 6 pages.
Written Opinion for International Application No. PCT/IB2017/ 053389 filed on Jun. 8, 2017 on behalf of SOFAR SPA. dated Oct. 6, 2017. 7 pages.
Written Opinion for International Application No. PCT/IB2017/ 057576 filed on Dec. 1, 2017 on behalf of SOFAR SPA. dated Feb. 22, 2018. 8 pages.
Written Opinion for International Application No. PCT/IB2017/ 057980 filed on Dec. 15, 2017 on behalf of SOFAR SPA. dated Mar. 19, 2018. 8 pages.
Written Opinion for International Application PCT/IB2015/052938 filed on Apr. 22, 2015 on behalf of SOFAR SPA. dated Jul. 31, 2015. 5 pages.
Zhang et al., "Isolated exopolysaccharides from lactobacillus rhamnosus GG alleviated adipogenesis mediated by TLR2 in mice" *Scientific reports*. vol. 6,Oct. 27, 2016.
Zheng, L. et al. "Regulation of colonic epithelial repair in mice by toll-like receptors and hyaluronic acid," Gastroenterology2009:137 2041-2051.
Aden K. et al., "Metabolic Functions of Gut Microbes Associate with Efficacy of Tumor Necrosis Factor Antagonists in Patients with Inflammatory Bowel Diseases" Gastroenterology, 2019, pp. 1279-1292.
Allegretti J. et al., "Short Chain Fatty Acid Profiles Are Altered by Fecal Microbiota Transplantation for the Treatment of Inflammatory Bowel Disease and Recurrent Clostridioides difficile Infection" *Gastroenterology*,2019, 2 pages.
Balzaretti S. et al., "The vaginal isolate Lactobacillus paracasei LPC-S01 (DSM 26760) is suitable for oral administration" *Frontiers in Microbiology*, vol. 6, art. 952,Sep. 2015 , 13 pages.
Banasiewicz T. et al., "Determination of butyric acid dosage based on clinical and experimental studies—a literature review" *Gastroenterology Review*,2020, pp. 119-125.
Borren N. et al., "Alterations in Fecal Microbiomes and Serum Metabolomes of Fatigues Patients With Quiescent Inflammatory Bowel Diseases" *Clinical Gastroenterology and Hepatology*, Mar. 2020, 35 pages.
Canadian Office Action for CA Application No. 2,923,392 filed on Sep. 5, 2014 on behalf of Sofar S.P.A. dated Jun. 1, 2020 4 pages.
Chassard C. et al., "Functional dysbiosis within the gut microbiota of patients with constipated-irritable bowel syndrome" *Alimentary Pharmacology and Therapeutics*, 2012, pp. 828-838.
Chilean Office Action for CL Application No. 201803193 filed on Sep. 5, 2014 dated Apr. 16, 2020 16 pages (English + Original).
Chinese Office Action for CN Application No. 201480049288 filed on Sep. 5, 2014 on behalf of SOFAR S.P.A. dated Sep. 16, 2020 8 pages (English + Original).
Colombian Office Action for CO Application No. NC2018/0010950 filed on Sep. 5, 2014 on behalf of SOFAR S.P.A. dated Jul. 27, 2020 11 pages (Partial English + Original).
Compare D. et al., "Lactobacillus casei DG and its postbiotic reduce the inflammatory mucosal response: an ex-vivo organ culture model of post-infectious irritable bowel syndrome" *BMC Gastroenterology*, 2017, 8 pages.
Costalos et al., "Enteral feeding of premature infants with *Saccharomyces boulardii*" *Early Human Development*, 74,(2003), 89-96.
Cremon C. et al., "Effect of Lactobacillus paracasei CNCM 1-1572 on symptoms, gut microbiota, short chain fatty acids, and immune activation In patients with irritable bowel syndrome: A pilot randomized clinical trial" *UEG Journal*, Sep. 2017, 10 pages.
Eurasian Notification of Grant for Application No. 201690464/28 filed on Sep. 5, 2014 on behalf of SOFAR S.P.A. dated Jun. 9, 2020 2 pages (English + Original).
Final Office Action for U.S. Appl. No. 14/916,959, filed Mar. 4, 2016 on behalf of SOFAR S.P.A. dated Aug. 21, 2020 48 pages.
Final Office Action for U.S. Appl. No. 15/305,470, filed Oct. 20, 2016 on behalf of SOFAR S.P.A. dated Jul. 10, 2020 21 pages.
Final Office Action for U.S. Appl. No. 16/301,361, filed Nov. 13, 2018 on behalf of SOFAR S.P.A. dated Sep. 21, 2020 11 pages.
Gargari G. et al., "Fecal Clostridiales distribution and short-chain fatty acids reflect bowel habits in irritable bowel syndrome" Environmental Microbiology, Sep. 2018, 31 pages.
Hustoft T. et al., "Effects of varying dietary content of fermentable short-chain carbohydrates on symptoms, fecal microenvironment,

(56) References Cited

OTHER PUBLICATIONS and cytokine profiles in patients with irritable bowel syndrome" Neurogastroenterology & Motility, Sep. 2016, 9 pages.
Irritable Bowel Syndrome—Wikipedia, dated Sep. 16, 2020. 33 pages, https://en.wikipedia.org/wiki/Irritable_bowel_syndrome.
Israeli Office Action for Application No. 244391 filed on Mar. 2, 2016 on behalf of Sofar S.P.A. dated Jun. 24, 2020 4 pages (English + Original).
Israeli Office Action for Application No. 269107 filed on Sep. 3, 2019 on behalf of SOFAR S.P.A. dated May 17, 2020 5 pages (English + Original).
Japanese Office Action for JP Application No. 2016564193 filed on Apr. 22, 2015 on behalf of Sofar S.P.A. dated Feb. 18, 2020 11 pages (English + Original).
Langhorst J. et al., "Distinct patterns of short-chain fatty acids during flare in patients with ulcerative colitis under treatment with mesalamine or a herbal combination of myrrh, chamomile flowers, and coffee charcoal: secondary analysis of a randomized controlled trial" European Journal of Gastroenterology & Hepatology, Feb. 2020, 6 pages.
Magnusson M. et al., "The Anti-inflammatory Immune Regulation Induced by Butyiale is Impaired in Inflamed Intestinal Mucosa from Patients with Ulcerative Colitis" Inflammation, Apr. 2020, 11 pages.
Mexican Office Action for MX Application No. MX/a/2016/002766 filed on Sep. 5, 2014 on behalf of SOFAR S.P.A. dated Aug. 13, 2020 10 pages (English + Original).
Pituch A. et al., "Butyric acid in functional constipation" *Przeglad Gastroenterologiczny*, 2013, 4 pages.
Pozuelo M. et al., "Reduction of butyrate and methane producing microorganisms in patients with Irritable Bowel Syndrome" *Nature Scientific Reports*, Apr. 2015, 12 pages.
Ringel-Kulka T. et al., "Short Chain Fatty Acids and Intestinal Transit in Patients With Irritable Bowel Syndrome and Healthy Controls" *AGA Abstracts*, May 2012, 1 page.
Scarpellini E. et al., "Efficacy of butyrate in the treatment of diarrhea-predominant irritable bowel syndrome" Digestive and Liver Disease, 2007, 4 pages.
Shi Y. et al., "Function and clinical implications of short-chain fatty acids in patients with refractory constipation ," Colorectal Disease Ireland, Feb. 2016, 8 pages.
Sun Q. et al., "Alterations in fecal short-chain fatty acids in patients with irritable bowel syndrome" *Systematic Review and Meta-Analysis*, Jan. 2019, 12 pages.
Third Chinese Office Action for CN Application No. 201480049296.4 filed on Sep. 5, 2014 on behalf of SOFAR S.P.A. dated Mar. 18, 2020 13 pages (English + Original).
Turco F. et al., Bacterial stimuli activate nitric oxide colonic mucosal production in diverticular disease. Protective effects of L. casei DG (Lactobacillus paracasei CNCM I-1572) UEG Journal, Nov. 2016, 10 pages.
Turco F. et al., "Enteroglial-derived S100B protein integrates bacteria-induced Toll-like receptor signalling in human enteric glial cells" GUT Neurogastroenterology, vol. 63, Mar. 2014, Originally Published online Jan. 3, 2013, 12 pages.
Tursi A. et al., "Assessment of Fecal Microbiota and Fecal Metabolome in Symptomatic Uncomplicated Diverticular Disease of the Colon" *J. Clin Gastroenterol* ,Oct. 2016, 4 pages.
Tursi A. et al., "Fecal Microbiota, Fecal and Urinary Metabolic Profiling and Symptomatic Uncomplicated Diverticular Disease of the Colon" *Digestive and Liver Disease*, 2017, 1 page.
Tursi A. et al., "Natural History of Symptomatic Uncomplicated Diverticular Disease: A 13-Year Prospective Study" *AGA Abstracts*, Apr. 2017, 1 page.
Zhuang M. et al., "Abundance of probiotics and butyrate-production microbiome manages constipation via short-chain fatty acids production and hormones secretion" Molecular Nutrition & Food Research, Jul. 2019, 41 pages.
Zhuang M. et al., "Systematic Review and Meta-analysis: Short-Chain Fatty Acid Characterization in Patients With Inflammatory Bowel Disease" *Inflammatory Bowel Disease*, Nov. 2019, 13 pages.

Mexican Office Action for MX Application No. MX/a/2016/002766 filed on Sep. 5, 2014 on behalf of SOFAR S.P.A. dated Mar. 18, 2021 10 pages (English + Original).
Screenshot from the web-archive of the Milano University, Nov. 23, 2015, 2 pages (English + Original).
Balzaretti S. et al., "A novel hetero-exopolysaccharide mediates the recognition of Lactobacillus paracasei DG by the immune system" Pharmabiotics Conference2015, Paris, Oct. 29-30, 2015,1 page.
Bienenstock J et al., "New insights into probiotic mechanisms" *Gut Microbes*, vol. 4 Issue 2, Apr. 2013, 7 pages.
Canadian Examination Search Report for CA Application No. 2,923,390 filed on Sep. 5, 2014 on behalf of SOFAR S.P.A. dated Jan. 26, 2021 4 pages.
Colombian Office Action for CO Application No. NC2018/0010954 filed on Nov. 1, 2018 on behalf of SOFAR S.P.A. dated Feb. 5, 2021 9 pages (Partial English + Original).
Colombian Office Action for CO Application No. NC2019/0007116 filed on Jul. 2, 2019 on behalf of SOFAR S.P.A. dated Jan. 15, 2021 19 pages (English + Original).
Declaration for the self-archiving of the doctoral thesis for "Exploring Lactohacillius Paracasei Probiosis and Metabolic Potential" by Balzaretti, Silvia Dated: Nov. 20, 2015 5 pages (English + Original).
Laws A. et al., "Determination of the structure and molecular weights of the exopolysaccharide produced by Lactobacillus acidophilus 5e2 when grown on different carbon feeds." *Carbohydr Res*. Feb. 4, 2008;343(2):301-7.
Notice of Allowance for U.S. Appl. No. 16/301,361, filed Nov. 13, 2018 on behalf of SOFAR S.P.A. dated Feb. 1, 2021 8 pages.
Paoluzi O.A., et al. "Low efficacy of levofloxacin-doxycycline-based third-line tripletherapy for Helicobacter pylori eradication in Italy." World Journal of Gastroenterology21: 6698-705, Jun. 2015.
Rosania R. et al. "Effect of probiotic or prebiotic supplementation on antibiotic therapy in the small intestinal bacterial overgrowth: a comparative evaluation." Curr Clin Pharmacol. May 2013; 8(2):169-72. 5 pages.
Cassard L. et al, "Individual strains of Lactobacillus paracasei differentially inhibit human basophil and mouse mast cell activation," Immunity, Inflammation, and Disease vol. 4, Issue 3., 2016. 11 Pages.
Mcfarland, et al., "Strain-Specificity and Disease-Specificity of Probiotic Efficacy: A Systematic Review and Meta-Analysis," Frontiers in Medicine, May 7, 2018. 14 Pages.
Ralf Jager et al., "Probiotic Administration Increases Amino Acid Absorption from Plant Protein: a Placebo-Controlled, Randomized, Double-Blind, Multicenter, Crossover Study," Probiotics and Antimicrobial Proteins, 2020. 10 Pages.
Smokvina T. et al. "Lactobacillus paracasei Comparative Genomics: Towards Species Pan-Genome Definition and Exploitation of Diversity," PLOS One, Jul. 19, 2013. 16 Pages.
Australian Examination Report for AU Application No. 2017263294 filed on May 15, 2017 on behalf of SOFAR S.P.A. dated Oct. 30, 2020 5 pages.
Chinese Decision of Rejection for CN Application No. 201480049296.4 filed on Sep. 5, 2014 on behalf of SOFAR S.P.A. dated Dec. 9, 2020 (English + Original) 12 pages.
Communication pursuant to Article 94(3) EPC for EP Application No. 14790322.3 filed on Sep. 5, 2014 on behalf of SOFAR S.P.A. dated Jan. 11, 2021 3 pages.
Cui Y. et al., "Revolution of Chronic Diarrhoea" China Medicine, Science, and Technology Publishing House, 1st edition, Jan. 2013, pp. 19-23 (Original + Partial Google Translation).
Israeli Office Action for IL Application No. 244391 filed on behalf of SOFAR S.P.A. dated Oct. 27, 2020 (English + Original) 4 pages.
Kay, RM., et al., "Dietary Fiber," J. of Lipid Research, v. 23, 1982. 221-242, 22 Pages.
Non-Final Office Action for U.S. Appl. No. 14/916,961, filed Mar. 4, 2016, on behalf of SOFAR S.P.A. dated Jan. 7, 2021. 22 Pages.
Restriction Requirement for U.S. Appl. No. 16/465,237, filed May 30, 2019 on behalf of SOFAR S.P.A. dated Dec. 21, 2020 8 pages.
Wang Y. et al., "Emerging Infectious Diseases" Science and Technology Documents Publishing House, 1st edition, Jan. 2006, pp. 310-312 (Original + Partial Google Translation).

(56) References Cited

OTHER PUBLICATIONS

Watanabe I. et al., "KT-11" *Food Style21*, vol. 17, No. 6, pp. 62-64,2013. 5 pages. (Machine Translation + Original).
Australian Examination Report for AU Application No. 2017367302 filed on Dec. 1, 2017 on behalf of SOFAR S.P.A. dated Jul. 23, 2021 4 pages.
Bacteriotherapy—Merriam-Webster Medical Dictionary, Archive Date: Apr. 26, 2016, 6 pages.
Bassi R. "Mesalazine + Lactobacillus paracasei CNCMI1572 vs Mesalazine alone in preventing recurrence of symptom of diverticular disease: a prospective, randomize, open-label study." *Colorectal Disease*, 2019 1 pages.
Bassi R. "Preventing recurrence of symptomatic diverticular disease of the colon: mesalazine with or without Lactobacillus case DG: a prospective randomized, open label study." European Society of Coloproctology, 2015, 1 page.
Brussow H. "Problems with the concept of gut microbiota dysbiosis" Microbial Biotechnology, vol. 13(2), 2020, pp. 423-434.
Canadian Office Action for CA Application No. 2,923,392 filed on Sep. 5, 2014 on behalf of SOFAR S.P.A. dated Apr. 1, 2021 4 pages.
Canani R. B. et al., "Potential beneficial effects of butyrate in intestinal and extraintestinal diseases" World Journal of Gastroenterology, vol. 17 No. 12, Mar. 2011, 10 pages.
Capsule (Pharmacy)—Wikipedia, the free encyclopedia, Archive Date: Apr. 10, 2016, 4 pages.
Chilean Office Action for CL Application No. 201901493 filed on Dec. 1, 2017 on behalf of SOFAR S.P.A. dated May 6, 2021 24 pages (English + Original).
Chinese Office Action for CN Application No. 201480049288X filed on Sep. 5, 2014 on behalf of SOFAR S.P.A. dated Aug. 12, 2021 (English + Original) 15 pages.
Chooi E. et al., "Chronic atrophic gastritis is a progressive disease: analysis of medical reports from Shanghai (1985-2009)" Singapore Med J, 2012, 53 (5), pp. 318-324.
Colledge H. "Atrophic Gastritis: Causes. Symptoms, & Treatment" *Healthline*, Sep. 2018, 5 pages.
Colombian Office Action for CO Application No. NC2018/0010950 filed on May 15, 2017 on behalf of SOFAR S.P.A. dated May 3, 2021 9 pages (English + Original).
Colombian Office Action for CO Application No. NC2018/0010954 filed on Jun. 2, 2019 on behalf of SOFAR S.P.A. dated Jun. 30, 2021 8 pages (Partial English + Original).
Colombian Office Action for Colombian Application No. NC2019/0006257 filed on Dec. 15, 2017 on behalf of Sofar S.P.A. dated May 13, 2021 3 pages (English + Original).
Communication pursuant to Article 94(3) EPC for EP Application No. 17817173.2 filed on Dec. 1, 2017 on behalf of SOFAR S.P.A. dated Sep. 29, 2021 6 pages.
De Backer A. I. et al., "Intestinal stenosis from mesenteric injury after blunt abdominal trauma" Eur. Radiol., 1999, pp. 1429-1431.
Dore J. et al., "The Human Intestinal Microbiota; From Phylogenetics to Functional Metagenomics" *Old Herborn University*, 2010, pp. 15-26.
Dysbiosis—Wikipedia, the free encyclopedia, Dated: Mar. 31, 2014 https://web.archive.org/web/20140331225522/http://en.wikipedia.org/wiki/Dysbiosis , 4 pages.
Eurasian Office Action for EA Application No. 202090097/28 filed on Sep. 5, 2014 on behalf of SOFAR S.P.A. dated Aug. 16, 2021 (English + Original) 10 pages.
Ferrario, et al., "Modulation of Fecal Clostridiales Bacteria and Butyrate by Probiotic Intervention with Lactobacillus paracasei DG Varies among Healthy Adults1-3" J. Nutritional Epidemiology, 144. Sep. 3, 2014. pp. 1787-1796. 10 Pages.
Final Office Action for U.S. Appl. No. 14/916,961, filed Mar. 4, 2016, on behalf of SOFAR S.P.A. dated Oct. 14, 2021. 26 Pages.
Gould M. et al., "Diabetic diarrhea" Current Gastroenterology Report, 2009, pp. 354-359 (Abstract only).
Gould, M., et al., "Diabetic Diarrhea," Current Gastroenterology Reports, 11: 354-359. Full paper. 2009. 7 Pages.
Haenel H. "Human Normal and Abnormal Gastrointestinal Flora" *American Journal of Clinical Nutrition*, vol. 23 No. 11, Nov. 1970, pp. 1433-1439.
Iebba V. et al., "Eubiosis and Dysbiosis: the two sides of the microbiota" *New Microbiologica*, vol. 39, 2016, pp. 1-12.
Jarbrink-Sehgal M. E. et al., "Symptomatic Diverticulosis is Characterized by Loose Stools" *Clinical Gastroenterology and Hepatology*, 14: 1763-1770, Dec. 2016, 9 pages.
John Hopkins Medicine—Fecal Transplantation (Bacteriotherapy), John Hopkins Division of Gastroenterology and Hepatology, Archive Date: Apr. 2016, 2 pages.
Koebnick C. et al., "Probiotic beverage containing Lactobacillus easel Shirota improves gastrointestinal symptoms in patients with chronic constipation" Can J Gastroenterol, vol. 17 No. 11, Nov. 2003, pp. 655-658.
Laval G. et al., "The use of steroids in the management of inoperable intestinal obstruction in terminal cancer patients: do they remove the obstruction?" Palliative Medicine, 2000, pp. 3-10.
Leonel, A.J., et al. "Butyrate: implications for intestinal function," Current Opinion in Clinical Nutrition and Metabolic Care 15(5): 474-479. 2012. 6 Pages.
Mangili G. et al., "Palliative care for intestinal obstruction in recurrent ovarian cancer: a multivariate analysis" *BMJ Journals*, 2005, 5 pages (Abstract Only).
Miceli E. et al., "Common Features of Patients with Autoimmune Atrophic Gastritis" *Clinical Gastroenterology and Hepatology*, 2012, pp. 812-814.
Non-Final Office Action for U.S. Appl. No. 14/916,959, filed Mar. 4, 2016 on behalf of SOFAR S.P.A. dated Apr. 13, 2021 33 pages.
Non-Final Office Action for U.S. Appl. No. 16/465,237, filed May 30, 2019, on behalf of SOFAR S.P.A. dated Jul. 9, 2021. 37 Pages.
Notice of Allowance for U.S. Appl. No. 15/305,470, filed Oct. 20, 2016 on behalf of SOFAR S.P.A. dated Jun. 1, 2021 15 pages.
Notice of Allowance for U.S. Appl. No. 15/305,470, filed Oct. 20, 2016, on behalf of SOFAR SPA. dated Sep. 8, 2021. 8 Pages.
Notice of Allowance for U.S. Appl. No. 16/301,361, filed Nov. 13, 2018, on behalf of SOFAR S.P.A. dated Aug. 4, 2021. 11 Pages.
Notice of Allowance for U.S. Appl. No. 16/301,361, filed Nov. 13, 2018 on behalf of SOFAR S.P.A. dated May 3, 2021 9 pages.
Restriction Requirement for U.S. Appl. No. 16/467,797, filed Jun. 7, 2019 on behalf of Sofar S.P.A. dated Jun. 15, 2021 6 pages.
Restriction Requirement for U.S. Appl. No. 17/090,669 filed Nov 5, 2020, on behalf of SOFAR S.P.A. dated Sep. 3, 2021. 7 Pages.
Rodriguez-Castro K. I. et al., "Clinical manifestations of chronic atrophic gastritis" Acta Biomed, vol. 89, 2018, pp. 88-92.
Scarpignato C. et al., "Management of colonic diverticular disease in the third millennium: Highlights from a symposium held during the United European Gastroenterology Week 2017" Therapeutic Advances in Gastroenterology, vol. 11, Mar. 2018, pp. 1-21.
Tsimmerman Y. S. "Eubiosis and Dysbiosis of Gastrointestinal Tract: Myths and Reality" *Perm State Medical Academy*, 2013, 27 pages.
Tuohy K.M. et al., "Survivability of a probiotic Lactobacillus easel in the gastrointestinal tract of healthy human volunteers and its impact on the faecal microflora" *Journal of Applied Mircrobiology*, 2007, pp. 1026-1032.
Wells D. "Gastritis Diet: What to Eat and What to Avoid" Healthline, Jul. 2020, 11 pages.
World Gastroenterology Organisation Global Guidelines "Probiotics and prebiotics" Feb. 2017, 35 pages.
Zhang, Z., et al., "Isolated exopolysaccharides from Lactobacillus rhamnosus GG alleviated adipogenesis mediated by TLR2 in mice," *Sci Rep* 6, 36083, Oct. 27, 2016. 13 Pages. https://doi.org/10.1038/srep36083.
Allowance of the Brazilian patent application BR 11 2016 005059 2 published in the Official Bulletin $n^{mt;epmuboubxmx}$2651 of Oct. 26, 2021 (Portuguese Only).
Canadian Office Action for CA Application No. 2,923,390 filed on Sep. 5, 2014 on behalf of SOFAR S.P.A. dated Nov. 29, 2021 5 pages.
Chinese Office Action for CN Application No. 201780029401.1 filed on May 15, 2017 on behalf of SOFAR S.P.A. dated Dec. 15, 2021 (English + Original) 24 pages.

(56) References Cited

OTHER PUBLICATIONS

Colombian Office Action for CO Application No. NC2018/0010950 filed on May 15, 2017 on behalf of SOFAR S.P.A. dated Oct. 14, 2021 (Partial English + Original) 9 pages.

Colombian Office Action for CO Application No. NC2019/0007116 filed on Jul. 2, 2019 on behalf of SOFAR S.P.A. dated Sep. 29, 2021 12 pages (English + Original).

Corrected Notice of Allowability for U.S. Appl. No. 15/305,470, filed Oct. 20, 2016 on behalf of SOFAR S.P.A. dated Jan. 10, 2022 4 pages.

Final Office Action for U.S. Appl. No. 14/916,959, filed Mar. 4, 2016 on behalf of SOFAR S.P.A. dated Dec. 29, 2021. 29 Pages.

Mexican Office Action for MX Application No. MX/a/2016/022766 filed on Sep. 5, 2014 on behalf of SOFAR S.P.A. dated Oct. 26, 2021 (Partial English + Original) 12 pages.

Non-Final Office Action for U.S. Appl. No. 16/467,797, filed Jun. 6, 2019 on behalf of SOFAR S.P.A. dated Dec. 14, 2021 35 pages.

Notice of Allowance for U.S. Appl. No. 15/305,470, filed Oct. 20, 2016, on behalf of SOFAR SPA. dated Nov. 3, 2021. 8 Pages.

Salvetti E. et al., "The Genus Lactobacillus: A Taxonomic Update" *Probiotics & Antimicro. Prot.*, Nov. 2012, vol. 4, pp. 217-226.

Et al., "Analysis of Lactic Acid Bacteria Protein Dissolution and Aroma Production Ability" Chinese Brew, vol. 33 No. 3, Dec. 31, 2014 (English Abstract + Original) 4 pages.

Azad M.D.A.K et al., "Immunomodulatory Effects of Probiotics on Cytokine Profiles" Biomed Research International, vol. 2018, Article ID 8063647, Oct. 2018, pp. 1-10.

Balzaretti S. et al., "The vaginal isolate Lactobacillus paracasei LPC-S01 (DSM 26760) is suitable for oral administration" Frontiers in Microbiology, vol. 6, Article 952 Sep. 2015, 13 pages.

Bedford A. et al., "Implications of butyrate and its derivatives for gut health and animal production" *Animal Nutrition*, vol. 4, 2018, pp. 151-159.

Borycka-Kiciak K. et al., "Butyric acid—a well-known molecule revisited" *Gastroenterology Rev*, vol. 12 No. 2, 2017, pp. 83-89.

Brunkwall L. et al., "Self-reported bowel symptoms are associated with differences in overall gut microbiota composition and enrichment of Blautia in a population-based cohort" *Journal of Gastroenterology and Hepatology*, vol. 36, (2021), pp. 174-180.

Cheng A. et al., "Polyphenols from blueberries modulate inflammation cytokines in LPS-induced RAW264.7 macrophages", *International Journal of Biological Macromolecules*, Elsevier vol. 69, Jun. 2014, pp. 382-387.

Cicenia, A. et al., "Postbiotic Activities of Lactobacilli-derived Factors", J Clin Gastroenterol, vol. 48, Supp. 1, Nov./Dec. 2014, S18-S22 (5 pages).

Connors J. et al., "The Role of Succinate in the Regulation of Intestinal Inflammation" *Nutrients*, vol. 11 No. 25, 2019, 12 pages.

Corrected Notice of Allowability for U.S. Appl. No. 15/305,470, filed Oct. 20, 2016, on behalf of SOFAR SPA. dated Feb. 25, 2022. 3 Pages.

Corrected Notice of Allowability for U.S. Appl. No. 16/465,237, filed May 30, 2019, on behalf of Sofar S.P.A. dated Jun. 22, 2022. 20 Pages.

Cui J. et al., "NMR-based metabonomics and correlation analysis reveal potential biomarkers associated with chronic atrophic gastritis" Journal of Pharmaceutical and Biomedical Analysis, vol. 132, 2017, pp. 77-86.

Feng W. et al., "Sodium Butyrate Attenuates Diarrhea in Weaned Piglets and Promotes Tight Junction Protein Expression in Colon in a GPR109A-Dependent Manner" *Cellular Physiology and Biochemistry*, vol. 47, 2018, pp. 1617-1629.

Gwiazdowska D. et al., "The impact of polyphenols on Bifidobacterium growth", Acta Biochimica Polonica, vol. 62 No. 4, Jan. 2015, 895-901. 8 pages.

Hajjar R. et al., "The role of butyrate in surgical and oncological outcomes in colorectal cancer" *American Journal of Physiology*, vol. 320, Jan. 2021, pp. G601-G608.

Hakansson A. et al., "Blueberry husks, rye bran and multi-strain probiotics affect the severity of colitis induced by dextran sulphate sodium" *Scandinavian Journal of Gastroenterology*, vol. 44 No. 10, Jan. 2009, pp. 1213-1225.

Hurst N.R. et al., "The Short Chain Fatty Acids, butyrate and Propionate, have Differential Effects on the Motility of the Guinea Pig Colon" *Neurogastroenterol Motil.*, vol. 26 No. 11, Nov. 2014, pp. 1586-1596.

International Preliminary Report on Patentability for International Application No. PCT/IB2020/058774 filed on Sep. 21, 2020 on behalf of SOFAR S.P.A. dated Mar. 15, 2022 16 pages.

International Preliminary Report on Patentability for International Application No. PCT/IB2020/058769 filed on Sep. 21, 2020 on behalf of SOFAR S.P.A. dated Mar. 15, 2022 6 pages.

International Preliminary Report on Patentability for International Application No. PCT/IB2020/058777 filed on Sep. 21, 2020 on behalf of SOFAR S.P.A. dated Mar. 15, 2022 6 pages.

International Preliminary Report on Patentability for International Application No. PCT/IB2020/058778 filed on Sep. 21, 2020 on behalf of SOFAR S.P.A. dated Mar. 15, 2022 6 pages.

International Preliminary Report on Patentability for International Application No. PCT/IB2020/060412 filed on Nov. 5, 2020 on behalf of SOFAR S.P.A. dated May 10, 2022 7 pages.

International Search Report and Written Opinion for International Application No. PCT/IB2020/058778 filed on Sep. 21, 2020 on behalf of SOFAR S.P.A. dated Feb. 18, 2021 8 pages.

International Search Report and Written Opinion for International Application No. PCT/IB2020/058769 filed on Sep. 21, 2020 on behalf of SOFAR S.P.A. dated Feb. 18, 2021 8 pages.

International Search Report and Written Opinion for International Application No. PCT/IB2020/058774 filed on Sep. 21, 2020 on behalf of SOFAR S.P.A. dated Dec. 8, 2020 8 pages.

International Search Report and Written Opinion for International Application No. PCT/IB2020/058777 filed on Sep. 21, 2020 on behalf of SOFAR S.P.A. dated Apr. 20, 2021 26 pages.

International Search Report and Written Opinion for International Application No. PCT/IB2020/060412 filed on Nov. 5, 2020 on behalf of SOFAR S.P.A. dated Mar. 4, 2021 10 pages.

Koradia et al., "Probiotic and cranberry supplementation for preventing recurrent uncomplicated urinary tract infections in premenopausal women: a controlled pilot study" *Expert Review of Anti-Infective Therapy*, vol. 17 No. 9, Sep. 2019, pp. 733-740.

Krokowicz L. et al., "Sodium butyrate and short chain fatty acids in prevention of travellers, diarrhoea—a randomized prospective study" *Travel Medicine and Infectious Disease*, Aug. 2013, 17 pages.

Lacombe A. et al., "The potential of berries to serve as selective inhibitors of pathogens and promoters of beneficial microorganisms" *Food Quality and Safety*, vol. 1 No. 1, Mar. 2017, pp. 3-12.

Le Noci V. et al., "Modulation of Pulmonary Microbiota by Antibiotic or Probiotic Aerosol Therapy: A Strategy to Promote Immunosurveillance against Lung Metastases" *Cell Reports*, vol. 24 No. 13, Sep. 2018, pp. 3528-3538.

Metagenomics—Wikipedia, the free encyclopedia, Dated: May 16, 2013 https://web.archive.org/web/20130516095714/https://en.wikipedia.org/wiki/Metagenomics , 16 pages.

Mileo A.M et al., "Polyphenols: Immunomodulatory and Therapeutic Implication in Colorectal Cancer" *Frontiers in Immunology*, vol. 10, article 729 Apr. 2019, 10 pages.

Milko Radicioni, et al., "Survival of L. easel DG (CNCMI572) in the gastrointestinal tract of a healthy paediatric population", European Journal of Nutrition, *Steinkopff Verlag*, vol. 58 No. 8, Nov. 2018, 3161-3170. 10 pages.

Nanau R.M. et al., "Nutritional and Probiotic Supplementation in Colitis Models" *Digestive Diseases and Sciences, Kluwer Academic Publishers-Plenum Publishers*, vol. 57 No. 11, Jun. 2012, pp. 2786-2810.

Non-Final Office Action for U.S. Appl. No. 17/090,669 filed Nov. 5, 2020, on behalf of SOFAR S.P.A. dated Feb. 17, 2022. 45 Pages.

Notice of Allowance for U.S. Appl. No. 15/305,470, filed Oct. 20, 2016 on behalf of SOFAR S.P.A. dated Feb. 15, 2022 6 pages.

Notice of Allowance for U.S. Appl. No. 15/305,470, filed Oct. 20, 2016, on behalf of SOFAR SPA. dated Jun. 9, 2022. 11 Pages.

(56) References Cited

OTHER PUBLICATIONS

Notice of Allowance for U.S. Appl. No. 16/301,361, filed Nov. 13, 2018, on behalf of SOFAR S.P.A. dated Mar. 30, 2022. 11 Pages.
Notice of Allowance for U.S. Appl. No. 16/465,237, filed May 30, 2019, on behalf of SOFAR S.P.A. dated Jun. 1, 2022. 15 Pages.
Notice of Allowance for U.S. Appl. No. 16/467,797, filed Jun. 7, 2019 on behalf of SOFAR S.P.A. dated Jul. 15, 2022 13 pages.
Qin J. et al., "A human gut microbial gene catalogue established by metagenomic sequencing" Nature, vol. 46, Mar. 2010, pp. 59-67.
Rajendran V.M. et al., "Na-H Exchanger Isoform-2 (NHE2) Mediates Butyrate-dependent Na+ Absorption in Dextran Sulfate Sodium (DSS)-induced Colitis" Journal of Biological Chemistry, vol. 290 No. 42, Oct. 2015, 25487-25496. 10 pages.
Saez-Lara M.J. et al., "The Role of Probiotic Lactic Acid Bacteria and Bifidobacteria in the Prevention and Treatment of Inflammatory Bowel Disease and Other Related Diseases: A systematic review of randomized human clinical trials" Biomed Research International, vol. 2015, article ID 505878 Jan. 2015, pp. 1-15.
Tsilingiri, K. et al., "Probiotic and postbiotic activity in health and disease: activity comparison on a novel polarised ex-vivo organ culture method", Gut 2012; 61:1007-1015 (9 pages).
Vicariotto, Franco "Effectiveness of an association of a cranberry dry extract, D-mannose, and the two microorganisms Lactobacillus plantarum LP01 and Lactobacillus paracasei LPC09 in women affected by cystitis: a pilot study." J Clin Gastroenterol, Nov. 2014, vol. 48, Supp. 1,: S96-S101. 6 pages.
Xu J. et al., "Intake of blueberry fermented by lactobacillus plantarum affects the guy microbiota of L-name treated rats" Evidence-Based Complementary and Alternative Medicine, vol. 2013, article ID 809128, Jan. 2013, pp. 1-9.
Xue H. Lactose-Induced Chronic Diarrhea Results from Abnormal Luminal Microbial Fermentation and Disorder of Ion Transport in the Colon Frontiers in Physiology, vol. 11, article 877, Jul. 2020, pp. 1-14.
Yehua Yan, et al., "Mixed fermentation of blueberry pomace with L. rhamnosus GG and L. plantarum-1: Enhance the active ingredient, antioxidant activity and health-promoting benefits", Food and Chemical Toxicology, vol. 131, 2019, 8 pages.
Yoshida Y. et al., "Oral administration of Lactobacillus plantarum Lq80 and Megasphaera elsdenii iNP-001 induces efficient recovery from mucosal atrophy in the small and the large intestines of weaning piglets" Animal Science Journal, vol. 80, 2009, pp. 709-715.
Zhernakova A. et al., "Population-based metagenomics analysis reveals markers for gut microbiome composition and diversity" Science, vol. 352, Apr. 2016, 15 pages.
Patel R. M. et al., "Therapeutic Use of Prebiotics, Probiotics, and Postbiotics to Prevent Necrotizing Enterocolitis: What is the Current Evidence?" Clin Perinatol, vol. 40, Mar. 2013, pp. 1-20.
Santigosa E. et al., "Modifications of intestinal nutrient absorption in response to dietary fish meal replacement by plant protein sources in sea bream (Sparus aurata) and rainbow trout (Onchorynchus mykiss)" Fish Nutrition Research Laboratory, 2011, 38 pages.
Cure—Wikipedia, the free encyclopedia. Date: May 12, 2013 4 pages https://web.archive.org/web/20130512085159/https://en.wikipedia.org/wiki/Remission (medicine).
De Almada C. N. et al., "Paraprobiotics: Evidences on their ability to modify biological responses, inactivation methods and perspectives on their application in foods" Trends in Food Science & Technology, vol. 58, 2016, pp. 96-114.
Final Office Action for U.S. Appl. No. 17/090,669, filed Nov. 5, 2020 on behalf of SOFAR S.P.A., dated Nov. 9, 2022. (15 pages).
Lee Y. K. et al., "Handbook of Probiotics and Prebiotics" Wiley, 2009, Excerpt: 3 pages.
Non-Final Office Action for U.S. Appl. No. 14/916,959, filed Mar. 4, 2016, on behalf of SOFAR S.P.A. dated Sep. 30, 2022. 34 Pages.
Non-Final Office Action for U.S. Appl. No. 16/467,797, filed Jun. 7, 2019 on behalf of SOFAR S.P.A. dated Sep. 14, 2022. 5 Pages.
Non-Final Office Action for U.S. Appl. No. 14/916,961, filed Mar. 4, 2016 on behalf of SOFAR S.P.A. dated Aug. 29, 2022. 25 Pages.
Notice of Allowance for U.S. Appl. No. 16/465,237, filed May 30, 2019 on behalf of SOFAR S.P.A. dated Nov. 2, 2022 13 pages.
Patel R. M. et al., "Therapeutic Use of Prebiotics, Probiotics, and Postbiotics to Prevent Necrotizing Enterocolitis: What is the Current Evidence?" Clin Perinatal, vol. 40, Mar. 2013, pp. 1-20.
Poortmans J. R. et al., "Protein metabolism and physical training: any need for amino acid supplementation?" Nutrire, vol. 41 No. 21, 2016, pp. 1-17.
Santigosa E. et al., "Modifications of intestinal nutrient absorption in response to dietary fish meal replacement by plant protein sources in sea bream (Spares aurata) and rainbow trout (Onchorynchus mykiss)" Fish Nutrition Research Laboratory, 2011, 38 pages.
Tomar S. K. et al., "Role of probiotics, prebiotics, synbiotics, and postbiotics in inhibition of pathogens" The Battle Against Microbial Pathogens: Basic Science, Technological Advances and Educational Programs, 2015, pp. 717-732.
Tsilingiri K. et al., "Postbiotics: what else?" Beneficial Microbes, vol. 4 No. 1, Mar. 2013, pp. 101-107 (Abstract Only).
WHO Technical Report Series 935—Protein And Amino Acid Requirements in Human Nutrition, 2007, 284 pages.
Arumugam, M., et al., "Enterotypes of the human gut microbiome," Nature 473:174-180. May 12, 2011. 16 Pages, https://doi.org/10.1038/nature09944.
Brazilian Office Action for BR112018074795 filed on Jun. 8, 2017 on behalf of SOFAR S.P.A. dated Sep. 22, 2022 6 pages (Partial English Translation + Original).
Canadian Office Action for CA Application No. 2,923,390 filed on Mar. 4, 2016 on behalf of SOFAR S.P.A. dated Nov. 3, 2022, 4 pages.
Colombian Office Action for NC2018/0010954 filed on Nov. 1, 2018 on behalf of SOFAR S.P.A. dated Jan. 6, 2022 (English Translation + Original) 8 pages.
Final Office Action for U.S. Appl. No. 14/916,961, filed Mar. 4, 2016 on behalf SOFAR S.P.A., dated Dec. 19, 2022, 19 pages.
Hamady, M., et al., "Microbial community profiling for human microbiome projects: Tools, techniques, and challenges," Genome Res. 19: 1141-1152. Apr. 21, 2009. 12 Pages. doi:10.1101/gr.085464.108.
Mayo Clinic, "Diabetic neuropathy", Mayo Foundation for Medical Education and Research, 2022, downloaded from https://www.mayoclinic.org/diseases-conditions/diabetic-neuropathy/symptoms-causes/syc-20371580, 3 pages.
Riesenfeld, C.S., "Metagenomics: Genomic Analysis of Microbial Communities," Annu. Rev. Genet. 38: 525-52. Jul. 14, 2004. 30 Pages, doi: 10.1146/annurev.genet.38.072902.091216.
Yu, K., et al., "Metagenomic and Metatranscriptomic Analysis of Microbial Community Structure and Gene Expression of Activated Sludge," PLoS One 7(5): e38183. 2012. 13 Pages, https://doi.ora/10.1371/journal.pone.0038183.
Annex to Summons for EP Application No. 17 742 849.7 filed on June 8, 2017 on behalf of SOFAR S.P.A., dated Feb. 23, 2023, 8 pages.
Annibale, B. et al., "Efficacy of Lactobacillus paracasei sub. paracasei F19 on abdominal symptoms in patients with symptomatic uncomplicated diverticular disease: A pilot study", Minerva Gastroentroloica E Dietologica, vol. 57, No. 1, Mar. 2011, 12 pages.
Distrutti, Eleanora et al., "Gut microbiota role in irritable bowel syndrome: New therapeutic strateies", World J Gastroenterol, Feb. 21, 2016, 22(7), 2219-2241 24 pages.
Final Office Action for U.S. Appl. No. 14/916,959 filed Mar. 4, 2016 on behalf of SOFAR S.P.A., dated Mar. 27, 2023 (31 pages).
Final Office Action for U.S. Appl. No. 16/467,797 filed Jun. 7, 2019 on behalf of SOFAR S.P.A., dated Mar. 3, 2023. (9 pages).
Healthy Definition and Meaning—Merriam-Webster Dictionary, downloaded Feb. 19, 2023, https://www.merriam-webster.com/dictionary/health , 16 pages.
Kim, H.J. et al., "A randomized controlled trial of a probiotic combination VSL# 3 and placebo in irritable bowel syndrome with bloating", Neurogastroenterol Motil, Oct. 2005, 17(5), 687-696, (10 pages).
Lamiki, Pepu et al., "Probiotics in Diverticular Disease of the Colon: an Open Label Study", J. Gastrointestin Liver Dis, Mar. 2010, Vo. 19, No. 1, pp. 31-36. (6 pages).

(56) References Cited

OTHER PUBLICATIONS

Notice of Allowance for U.S. Appl. No. 17/090,669 filed Nov. 5, 2020 on behalf of SOFAR S.P.A., dated Apr. 24, 2023. (7 pages).
Summons to attend oral proceedings pursuant to Rule 115(1) EPC for EP Application No. 17 742 849.7 filed on Jun. 8, 2017 on behalf of SOFAR S.P.A., dated Feb. 23, 2023, 2 pages.
U.S. National Library of Medicine, Search of: "accepts healthy volunteers"—List Results, ClinicalTrials.gov, downloaded Feb. 19, 2023, https://clinicaltrials.gov/ct2/results?cond=&term=healthy&cntry=&sta. 4 pages.
Xu, J., "Microbial ecology in the age of genomics and metagenomics: concepts, tools, and recent advances" Molecular Ecology, Jun. 2006, 15(7), 1713-1731 (19 pages).

* cited by examiner

MEDICAL USE OF PROBIOTICS

CROSS-REFERENCE TO RELATED APPLICATIONS

This application is a 371 National Stage application of International PCT Application No. PCT/162017/053389, filed Jun. 8, 2017, and claims priority to Italian Patent Application No. 102016000058515, filed Jun. 8, 2016, both of which are incorporated herein by reference in their entirety.

TECHNICAL FIELD

The present invention relates to the use of a composition based on bacteria, preferably of the genus *Lactobacillus* and/or *Bifidobacterium*, and/or yeasts and/or other microorganisms, taken singularly or in combination, for treating the symptoms of and/or treating Irritable Bowel Syndrome (IBS) or also similar pathologies affecting the gastrointestinal apparatus.

STATE OF THE ART

Gastrointestinal disorders are a very widespread condition and represent a major portion of the costs that states have to bear for public health as well having a strong negative impact on the quality of life of affected individuals.

In particular, Irritable Bowel Syndrome (IBS), or irritable colon syndrome, is one of the most common gastrointestinal disorders. It affects around 15-20% of the population in the United States and Europe and the abdominal discomfort or pain often correlated with it is associated with changes in intestinal habits.

IBS has traditionally been considered a disorder of the psychological sphere associated with motor anomalies of the intestine and visceral hyperalgesia. Despite the lack of clear anomalies at the digestive level, the recent application of quantitative morphological and molecular techniques has revealed alterations within the gastrointestinal mucosa or in the lumen at the tissue, cellular and molecular level in a large percentage of patients suffering from IBS.

In light of the foregoing, there is a strongly felt need for new and/or alternative therapeutic solutions which may alleviate the symptoms associated with this pathology and/or treat the pathology.

SUMMARY OF THE INVENTION

The Applicant has found that the administration, or use, of a composition based on bacteria and/or yeasts and/or other microorganisms, taken singularly or in combination, is a solution to the above-mentioned need. In particular, bacteria belonging to a genus selected from among:

*Lactobacillus, Bifidobacterium, Bacillus, Propionibacterium, Streptococcus, Lactococcus, Aerococcus* and *Enterococcus*, preferably bacteria belonging to the genus *Lactobacillus* and/or *Bifidobacterium*, have shown to be particularly effective.

In fact, it has been surprisingly demonstrated by the Applicant that the administration, or use, preferably in oral form, of a composition based on bacteria belonging to the genus *Lactobacillus* and/or *Bifidobacterium*, in particular a probiotic composition comprising the bacterial species *Lactobacillus paracasei*, alleviates the symptoms associated with IBS, in particular by improving the abdominal pain and discomfort associated therewith.

Furthermore, the use of a composition based on these bacteria brings about:

an increase, in general at the level of the intestinal microbiota, in the bacterial population of the genus *Lactobacillus* and, at the same time, a significant reduction in the bacterial population belonging to the genus *Ruminococcus*, a pathobiont normally associated with IBS;

an increase in the intestinal concentration of short-chain fatty acids, in particular butyric and/or acetic acid; and a reduction in proinflammatory cytokines, in particular IL-6 and/or IL-15.

BRIEF DESCRIPTION OF THE DRAWINGS

The present invention will be described in detail below, also with the aid of the following figures and with examples that are not intended to have any limiting character.

In particular.

DETAILED DESCRIPTION OF PREFERRED EMBODIMENTS OF THE INVENTION

Figure 1:
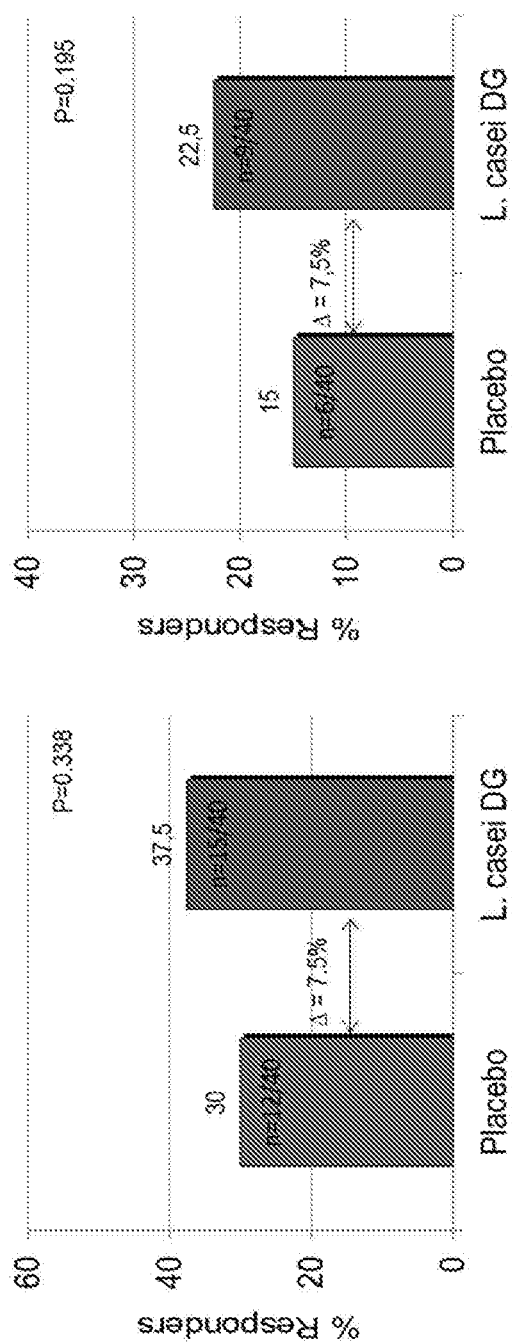
FIG. 1 shows how the intake of *L. casei* DG® improves abdominal pain and the IBS degree-of-relief.

A first aspect of the present invention relates to a composition based on bacteria and/or yeasts and/or other microorganisms, taken singularly or in combination, for use in the treatment of the symptoms of and/or for treating Irritable Bowel Syndrome (IBS) or also similar pathologies affecting the gastrointestinal apparatus.

Preferably, the composition—also defined probiotic composition or probiotic—comprises the bacteria belonging to the genus *Lactobacillus* and/or *Bifidobacterium*.

The symptoms against which the above-described composition has demonstrated benefits are preferably represented by abdominal pain and discomfort associated with IBS.

Preferably, the treatment of the symptoms of and/or for the treatment of Irritable Bowel Syndrome (IBS) or also similar pathologies affecting the gastrointestinal apparatus is associated with an increase, in general at the level of the intestinal microbiota, in the bacterial population of the genus *Lactobacillus* and/or, preferably at the same time, a significant reduction in the bacterial population belonging to the genus *Ruminococcus*, i.e. a pathobiont normally associated with IBS.

Therefore, the effectiveness in the treatment of IBS and the symptoms thereof is correlated with the increase, in general at the level of the intestinal microbiota, in the bacterial population of the genus *Lactobacillus* and/or, preferably at the same time, a significant reduction in the bacterial population belonging to the genus *Ruminococcus*.

According to a further preferred aspect of the invention, the treatment of the symptoms of and/or for treating Irritable Bowel Syndrome (IBS) or also similar pathologies affecting the gastrointestinal apparatus is associated with an increase in the intestinal concentration of short-chain fatty acids, in particular butyric and/or acetic acid and/or with a reduction in proinflammatory cytokines, in particular IL-6 and/or IL-15.

In this context, the definition of "probiotic" is the one formulated by a group of experts jointly convened in 2001 by the FAO and the WHO: "Live microorganisms which when administered in adequate amounts confer a health benefit on the host". In particular, in Italy, the Ministry of Health has defined probiotics as "microorganisms which demonstrate to be able, once ingested in sufficient amounts, to exert functions that are beneficial for the body", substantially echoing the definition of the two above-mentioned organisations.

Preferably, the bacteria of the genus *Lactobacillus* belong to at least one of the following species: *Lactobacillus paracasei, Lactobacillus acidophilus, Lactobacillus rhamnosus, Lactobacillus amylolyticus, Lactobacillus amylovorus, Lactobacillus alimentarius, Lactobacillus aviaries, Lactobacillus brevis, Lactobacillus buchneri, Lactobacillus casei, Lactobacillus cellobiosus, Lactobacillus corynifor-mis, Lactobacillus crispatus, Lactobacillus curvatus, Lactobacillus delbrueckii, Lactobacillus farciminis, Lactobacillus fermenturn, Lactobacillus gaffinarum, Lactobacillus gassed, Lactobacillus helveticus, Lactobacillus hilgardii, Lactobacillus johnsonii, Lactobacillus kefiranofaciens, Lactobacillus kefiri, Lactobacillus mucosae, Lactobacillus panis, Lactobacillus coffinoides, Lactobacillus paraplantarum, Lactobacillus pentosus, Lactobacillus plantarum, Lactobacillus pontis, Lactobacillus reuteri, Lactobacillus sakei, Lactobacillus salivarius* and *Lactobacillus sanfranciscensis*.

Preferably, the bacteria of the genus *Bifidobacterium* belong to at least one of the following species: *B. animalis, B. bifidum, B. breve, B. infantis, B. longum, B. adolescentis, B. catenulatum, B. angulatum, B. asteroides, B. bourn, B. choerinum, B. coryneforme, B. cuniculi, B. denticolens, B. dentium, B. gallicum, B. gaffinarum, B. indicum, B. inopinatum, B. lactis, B. magnum, B. merycicum, B. minimum, B. pseudocatenulatum, B. pseudolongum, B. pullorum, B. ruminantium, B. saeculare, B. subtile, B. thermacidophilum, B. thermophilum* and *B. tsurumiense*.

The yeasts are preferably of the genus *Saccharomyces*, more preferably of the species *Saccharomyces cerevisiae* and/or *Saccharomyces boulardii*.

In general, the microorganisms comprised in the composition of the present invention are single microorganisms or combinations of any microbial species included in the QPS list of the EFSA.

The microorganisms of the composition of the present invention are preferably alive and the composition is therefore also definable as a probiotic.

Alternatively, the microorganisms of the composition are dead or in the form of a lysate or extract or fractions, and the composition is therefore also definable as a paraprobiotic.

In an alternative form, the composition further comprises the metabolic bioproducts generated by microorganisms defined as postbiotics and/or any other product of bacterial derivation.

Thus, the composition of the present invention is also a probiotic or a paraprobiotic or a postbiotic, known or presumed.

The bacteria within the composition can be taken singularly or in various combinations.

Preferably, the bacteria comprised in the composition are capable of surviving gastrointestinal transit and thus of reaching the colon alive and colonising it.

Preferably, the *Lactobacillus casei* is the strain DG® (*Lactobacillus paracasei* CNCM 1-1572). The bacterial strain *L. casei* DG® was deposited by SOFAR S.p.A. with the National Collection of Microorganism Cultures of the Pasteur Institute in Paris on May 5, 1995, with the deposit number CNCM 1-1572.

The bacteria within the composition are administered in a quantity ranging from 1 billion to 100 billion, preferably between 10 and 75 billion, more preferably between 15 and 50 billion, more preferably between 20 and 30 billion of viable bacterial cells per intake.

Preferably, intake takes place at least 1-2 times a day.

Administration can occur by any route. Preferably, the composition is taken orally, more preferably in the form of pills, capsules, tablets, granular powder, hard-shelled capsules, orally dissolving granules, sachets, lozenges or drinkable vials.

Alternatively, the composition of the invention is formulated as a liquid, for example as a syrup or beverage, or else it is added to food, for example to a yogurt, cheese or fruit juice.

Alternatively, the composition of the invention is formulated in a form capable of exerting a topical action, for example via enema.

The oral formulation of the composition of the present invention further comprises excipients generally accepted for the production of probiotic and/or pharmaceutical products.

Preferably, the composition comprises anti-caking agents, preferably silicon dioxide, magnesium stearate.

Preferably, the composition comprises coating agents, preferably gelatine, colouring agents.

In a further embodiment of the invention, the composition of the invention comprises vitamins, trace elements, preferably zinc or selenium, enzymes and/or prebiotic substances, preferably fructo-oligosaccharides (FOS), galacto-oligosaccharides (GOS), inulin, guar gum, both animal and vegetable proteins, antioxidants, plant extracts or combinations thereof.

Example

Figure 2:
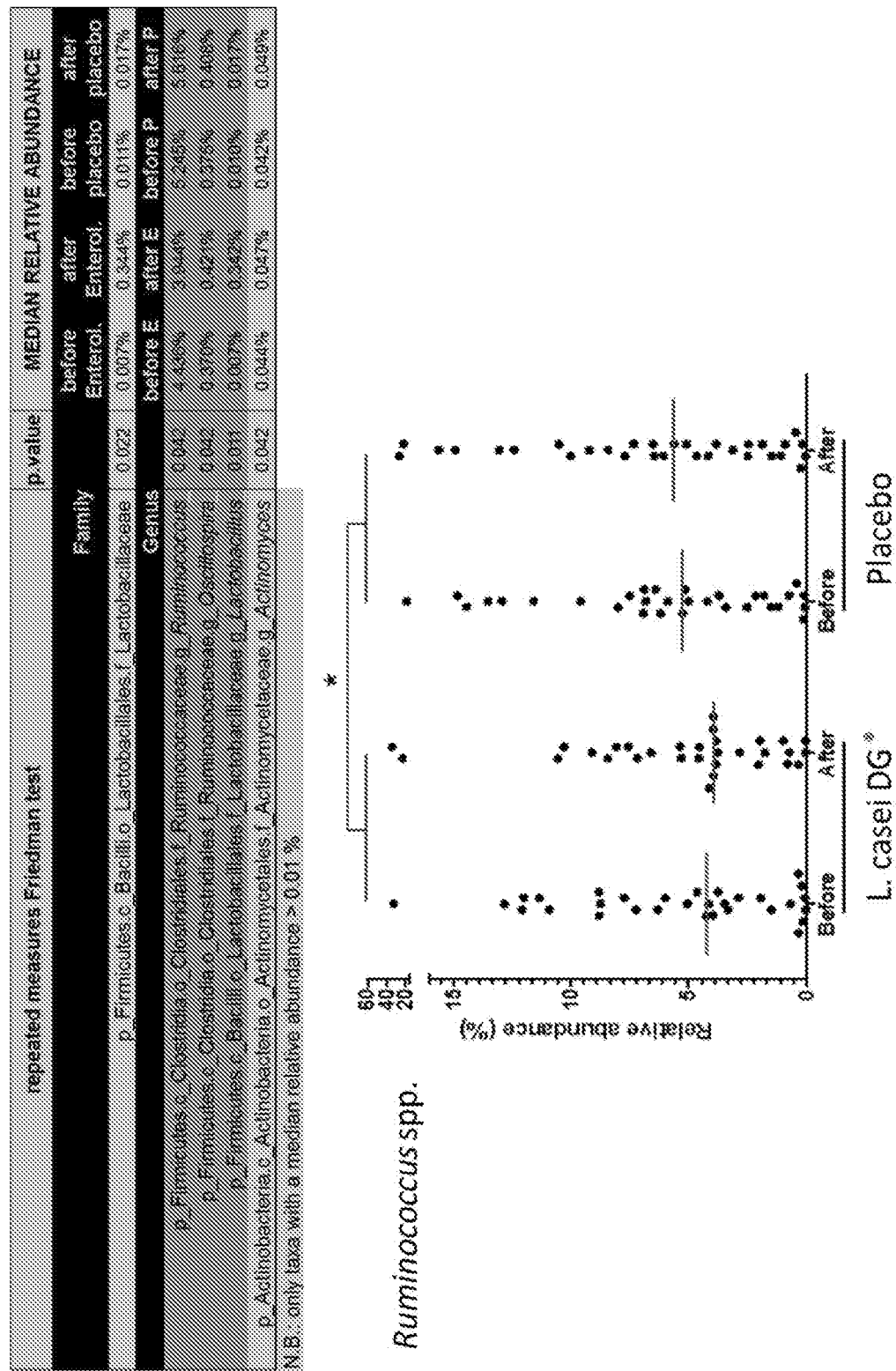
FIG. 2 shows how the intake of *L. casei* DG® induces a significant increase in the genus *Lactobacillus* and a significant reduction in the genus *Ruminococcus*.
Figure 3:
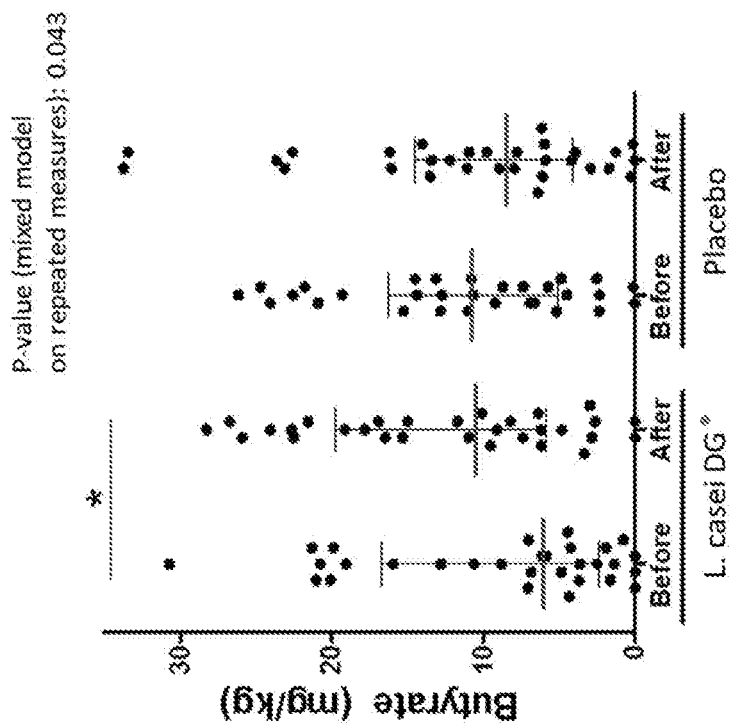
FIG. 3 shows how the intake of *L. casei* DG® induces a significant increase in short-chain fatty acids (butyric and acetic acids).
Figure 4:
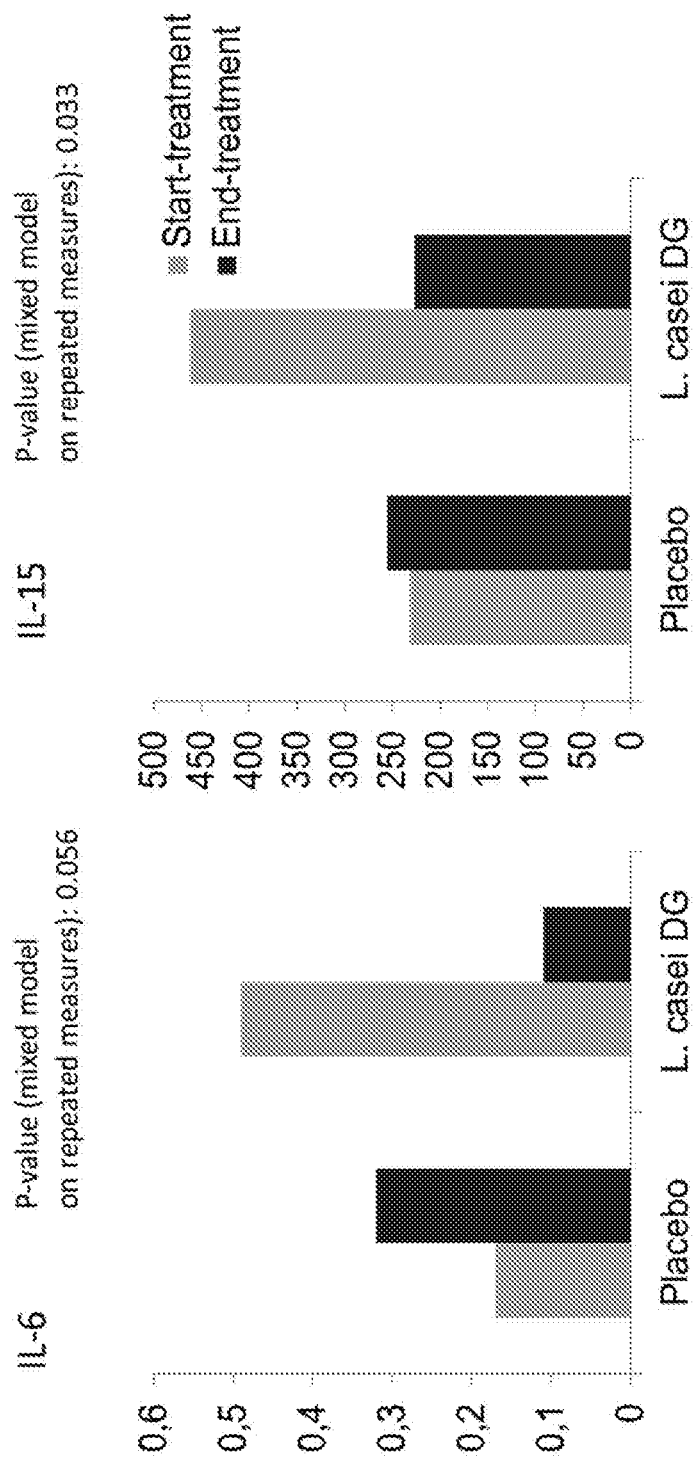
FIG. 4 shows how the intake of *L. casei* DG® induces a significant reduction in the proinflammatory cytokines IL-6 and IL-15.

In this context it was experimentally demonstrated, by means of a multi-centre randomized, double-blind placebo-controlled crossover clinical study, that the administration of the claimed composition to patients suffering from IBS:

improves abdominal pain and the IBS degree-of-relief (FIG. 1);

induces a significant increase in the genus *Lactobacillus* and a significant reduction in the genus *Ruminococcus* (FIG. 2);

induces a significant increase in short-chain fatty acids, in particular butyric and acetic acid (a drastic reduction in the concentrations thereof is typical of various pathological situations) (FIG. 3); and significantly reduces the proinflammatory cytokines IL-6 and IL-15 (FIG. 4).

Figure 5:
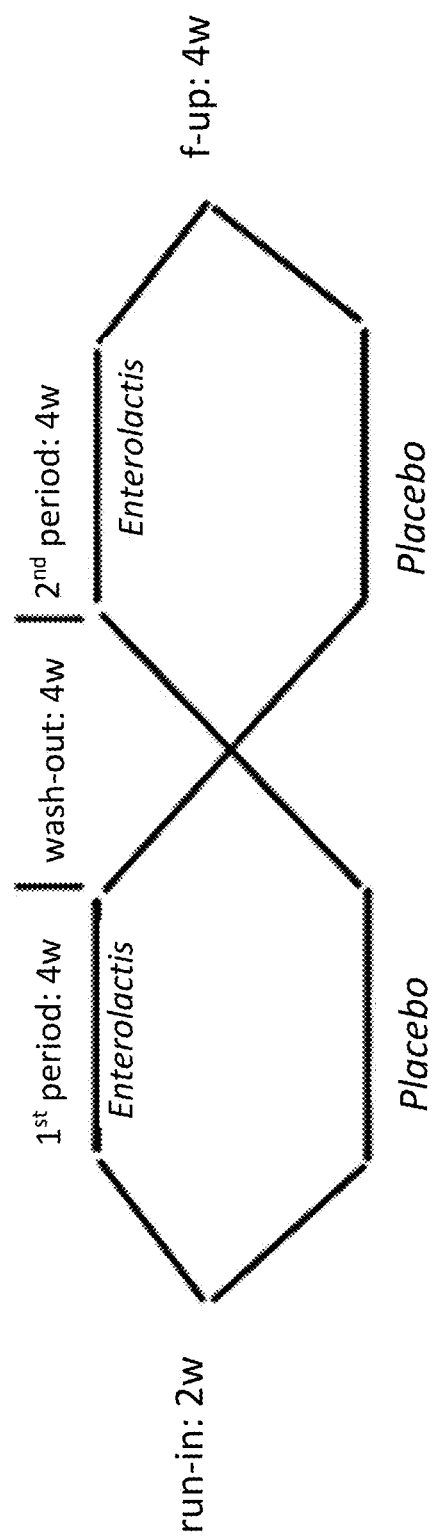
FIG. 5 shows a schematic illustration of the crossover design, coupled with a new-generation high-throughput DNA sequencing technology used in the clinical study reported in the instant disclosure.

The study was carried out in accordance with a crossover design, coupled with a new-generation high-throughput DNA sequencing technology (schematised in FIG. 5), which represents the best possible way to assess the changes in human intestinal flora, due to the great complexity and marked interindividual variability of the bacterial composition in the faecal microbial ecosystem.

In particular, the study comprised 5 stages:

Run-in period (2 weeks): the subjects did not take treatment A (Enterolactis® Plus), or treatment B (placebo), Treatment period 1 (4 weeks): the subjects took treatment A or treatment B.

Wash-out period (4 weeks): in which the subjects did not take treatment A or treatment B Treatment period 2 (4 weeks): the subjects took treatment B or treatment A.

Follow-up (4 weeks): the subjects did not take treatment A or treatment B

Treatments A and B can be the composition of the present invention, in the specific example Enterolactis® plus, or else the placebo. At the start of the treatment it was not known what the subject took and only at the end of the treatment, i.e. when the blind was broken, the sequence of intake was known.

Forty subjects suffering from IBS randomly received the composition of the present invention comprising *L. casei* DG® (Enterolactis® plus), 2 times a day for 4 weeks, or the equivalent product without bacteria (placebo).

The subjects of the study had the characteristics shown in Table I.

TABLE I

| Characteristics | Placebo/*L. casei* DG (n = 20) | *L. casei* DG/ Placebo (n = 20) |
|---|---|---|
| Age, years (±SD) | 44.55 (±12.98) | 37.35 (±11.25) |
| Female gender, n (%) | 15 (75%) | 11 (55%) |
| Ethnic origin | | |
| Caucasian, n (%) | 20 (100%) | 20 (100%) |
| Other, n (%) | 0 (%) | 0 (%) |
| 18S subtype (4) | | |
| 18S-D, n (%) | 6 (30%) | 8 (40%) |
| 18S-C, n (%) | 7 (35%) | 5 (25%) |
| 18S-M, n (%) | 1 (5%) | 2 (10%) |
| 18S-U, n (%) | 6 (30%) | 5 (25%) |
| Abdominal pain | 2.70 (±1.24) | 3.28 (±1.95) |

The compositions administered were the following:

Composition of the Invention:

*L. casei* DG® (*Lactobacillus paracasei* CNCM I-1572), at least 24 billion live cells anti-caking agents: SiO2 and magnesium stearate coating: food-grade gelatine and colouring agent E171

Composition of Placebo:

anti-caking agents: SiO2 and magnesium stearate coating: food-grade gelatine and colouring agent E171

The two compositions are aesthetically indistinguishable.

The total duration of the study was 18 weeks.

The parameters for assessing the effectiveness of the treatment are the following:

Abdominal pain/discomfort in the past 24 hours (the responders were defined as patients with a 30% reduction in the mean weekly abdominal pain and/or discomfort score, compared to the mean value of the run-in period, for at least 2 of the 4 weeks of the treatment period) using a daily 11-point numerical scale from "0" (none) to "10" (very severe)

IBS degree-of-relief in the past 7 days compared to the period preceding the beginning of the study (the responders were defined as patients with a score of 1="completely relieved" or 2="considerably relieved" for at least 2 of the 4 weeks of the treatment period), using a balanced 7-point ordinal scale, where 1="completely relieved", 4="unchanged" and 7="as bad as I can imagine"

Composition of the intestinal microbiota (analysed by means of an

Ion Torrent PGM, with nucleotide sequencing of portions of the gene encoding for the bacterial ribosomal RNA 16S subunit), of the short-chain fatty acids (SCFAs) (analysed by high-performance liquid chromatography, coupled with tandem mass spectrometry) and IgA and cytokines in stools (analysed by means of specific ELISA tests)

Daily stool frequency and consistency assessed using the Bristol scale

Overall satisfaction with the treatment assessed using the VAS scale

Hospital Anxiety and Depression Scale (HADS): seven points each for anxiety and depression, with a 4-point (0-3) Likert scale for each point, which provides a minimum score of 0 and a maximum score of 21 for each subscale Quality of life assessment using the validated Short-Form 12 Items Health Survey (SF-12), on a scale from 0 to 100

Intake of emergency drugs

The intake of *L. casei* DG® led to the following results:

As regards the abdominal pain and/or discomfort score, the percentage of responders was 37.5% (n=15) in the *L. casei* DG® group vs 30.0% (n=12) in the placebo group.

Similarly, as regards the IBS degree-of-relief, the percentage of responders was 22.5% (n=9) in the *L. casei* DG® group vs 15.0% (n=6) in the placebo group.

The stool concentrations of butyrate and acetate increased from the start to the end of the treatment with *L. casei* DG®, whereas they decreased during the placebo treatment.

The mean levels of IgA and IL-6 in stools decreased from the start to the end of the treatment with *L. casei* DG®, whereas they increased during the placebo treatment.

The mean value of IL-15 decreased during the treatment with *L. casei* DG®, whereas it increased with the placebo.

The scientific literature clearly indicates (as the studies are published in pre-eminent scientific journals, such as Gastroenterology, JCI and Nature) that high levels of IL-15 are associated with celiac disease, chronic inflammatory intestinal diseases, allergic disorders depending on intestinal antigens and also with severe diseases like lymphoma.

Finally, *L. casei* DG® induces a significant increase in the genus *Lactobacillus* and a statistically significant decrease in the genus *Ruminococcus*, which is a pathobiont normally associated with IBS. In healthy subjects, this genus is present in low quantities, whereas in subjects with IBS it is normally present in high quantities. The probiotic treatment reduces the number of cells of such bacteria. This genus can be seen as a sort of biological biomarker for IBS.

The results obtained at the end of the 18-week study period for each individual patient are summarised below:

*L. casei* DG® improves abdominal pain and the IBS degree-of-relief, even though the differences versus the placebo are not statistically significant;

*L. casei* DG® induces a significant increase in the genus *Lactobacillus* and a significant reduction in the genus *Ruminococcus*;

*L. casei* DG® induces a significant increase in short-chain fatty acids (butyric and acetic acid), which are linked to a series of beneficial activities on the intestinal mucosa; a drastic reduction in the concentrations thereof is typical of various pathological situations; and L. casei DG® induces a significant reduction in the proinflammatory cytokines IL-6 and IL-15.

The invention claimed is:

1. A method for treating abdominal pain and/or discomfort, comprising
administering to a patient suffering from Irritable Bowel Syndrome (IBS) a composition comprising *Lactobacillus paracasei* DG strain deposited with the deposit number CNCM 1-1572, the administering performed to treat the abdominal pain and/or discomfort associated with the IBS,
wherein the Irritable Bowel Syndrome (IBS) is selected from IBS-C and IBS-U.

2. The method according to claim 1, wherein said bacteria are alive or dead, as lysate or extract or fractions.

3. The method according to claim 1, wherein the bacteria are administered in a quantity ranging from 1 billion to 100 billion of alive bacteria for each administration.

4. The method of claim 3, wherein the bacteria are administered in a quantity ranging from 10-75 billion of alive bacteria for each administration.

5. The method of claim 4, wherein the bacteria are administered in a quantity ranging from 15-50 billion of alive bacteria for each administration.

6. The method of claim 5, wherein the bacteria are administered in a quantity ranging from 20-30 billion of alive bacteria for each administration.

7. The method according to claim 1, wherein said composition is formulated for oral use, or is formulated as a liquid, or is added to food, or is formulated in a form having a topical effect.

8. The method of claim 7, wherein the composition is formulated for oral use as pills, capsules, tablets, granular powders, hard-shelled capsules, soluble granules, bags, or drinkable vials.

9. The method of claim 7, wherein the composition is formulated as a syrup or a beverage.

10. The method of claim 7, wherein the composition is added to yogurt, cheese or fruit juice.

11. The method of claim 7, wherein the composition is formulated in the form of an enema.

12. The method according to claim 1, wherein the administration occurs at least 1-2 times per day.

13. The method of claim 1, wherein the composition further comprises yeasts and/or other microorganisms.

14. The method of claim 13, wherein the yeasts comprise *Saccharomyces cerevisiae* and/or *Saccharomyces boulardii*.

15. The method according to claim 13, wherein said yeast belongs to the genus *Saccharomyces*.

16. The method according to claim 13, wherein the composition further comprises metabolic products produced by said microorganisms defined as postbiotic and/or other bacteria-derived products.

* * * * *